United States Patent
Jarrahi et al.

(10) Patent No.: US 12,066,380 B2
(45) Date of Patent: Aug. 20, 2024

(54) METHODS AND SYSTEMS FOR DETECTING WATER STATUS IN PLANTS USING TERAHERTZ RADIATION

(71) Applicant: The Regents of the University of California, Oakland, CA (US)

(72) Inventors: Mona Jarrahi, Los Angeles, CA (US); Nezih Tolga Yardimci, Los Angeles, CA (US); Lawren Sack, Los Angeles, CA (US); Marvin Browne, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 181 days.

(21) Appl. No.: 17/755,523

(22) PCT Filed: Nov. 2, 2020

(86) PCT No.: PCT/US2020/058549
§ 371 (c)(1),
(2) Date: Apr. 29, 2022

(87) PCT Pub. No.: WO2021/087459
PCT Pub. Date: May 6, 2021

(65) Prior Publication Data
US 2023/0003642 A1  Jan. 5, 2023

Related U.S. Application Data

(60) Provisional application No. 62/928,900, filed on Oct. 31, 2019.

(51) Int. Cl.
*G01N 21/3581* (2014.01)
*A01G 25/16* (2006.01)
(Continued)

(52) U.S. Cl.
CPC ......... *G01N 21/3581* (2013.01); *A01G 25/16* (2013.01); *G01N 21/3563* (2013.01);
(Continued)

(58) Field of Classification Search
CPC .......... G01N 21/3581; G01N 21/3563; G01N 21/84; G01N 33/0098; G01N 2021/8466;
(Continued)

(56) References Cited

U.S. PATENT DOCUMENTS

| 6,173,604 | B1 | 1/2001 | Xiang et al. |
| 6,529,093 | B2 | 3/2003 | Ma |

(Continued)

FOREIGN PATENT DOCUMENTS

| CN | 107561032 A | 1/2018 |
| EP | 1804347 A1 | 7/2007 |

(Continued)

OTHER PUBLICATIONS

Gente et al., "Monitoring leaf water content with THz and sub-THz waves," Plant Methods, vol. 11, No. 15, 9 pages (Year: 2015).*
(Continued)

*Primary Examiner* — Kiho Kim
(74) *Attorney, Agent, or Firm* — KPPB LLP

(57) ABSTRACT

Methods and systems for determining water status in plant tissue are provided. A number of systems are capable of using terahertz signals to generate signals measuring total water content in plant tissue, including plant leaves. Using these signals, methods are capable of determining water status variables, including water mass per leaf area, relative water content, and leaf water potential, which can aid in agricultural, ecological, and environmental health, such as dehydration and drought stress of plants.

18 Claims, 9 Drawing Sheets
(6 of 9 Drawing Sheet(s) Filed in Color)

(51) Int. Cl.
  *G01N 21/3563* (2014.01)
  *G01N 21/84* (2006.01)
  *G01N 33/00* (2006.01)
  *G06Q 10/04* (2023.01)
  *G06Q 50/02* (2012.01)

(52) U.S. Cl.
  CPC ......... *G01N 21/84* (2013.01); *G01N 33/0098* (2013.01); *G06Q 10/04* (2013.01); *G06Q 50/02* (2013.01); *G01N 2021/8466* (2013.01); *G01N 2201/06113* (2013.01); *G01N 2201/127* (2013.01)

(58) Field of Classification Search
  CPC ... G01N 2201/06113; G01N 2201/127; G01N 2021/1797; G01N 2201/103; G01N 21/3554; G01N 21/3586; A01G 25/16; G06Q 10/04; G06Q 50/02
  See application file for complete search history.

(56) References Cited

U.S. PATENT DOCUMENTS

| | | |
|---|---|---|
| 7,321,275 B2 | 1/2008 | Chou et al. |
| 7,515,801 B2 | 4/2009 | McCaughan et al. |
| 7,599,409 B2 | 10/2009 | Nishizawa et al. |
| 7,710,637 B2 | 5/2010 | Ikari et al. |
| 7,834,722 B2 | 11/2010 | Millet |
| 7,915,641 B2 | 3/2011 | Otsuji et al. |
| 8,450,687 B2 | 5/2013 | Lampin et al. |
| 8,466,528 B2 | 6/2013 | Okamoto et al. |
| 8,514,403 B2 | 8/2013 | Ogawa et al. |
| 8,581,784 B2 | 11/2013 | Nagel |
| 8,610,094 B2 | 12/2013 | Kim et al. |
| 8,649,414 B2 | 2/2014 | Park |
| 8,730,567 B2 | 5/2014 | Kim et al. |
| 9,804,026 B2 | 10/2017 | Jarrahi et al. |
| 9,859,079 B2 | 1/2018 | Jarrahi et al. |
| 10,120,263 B2 | 11/2018 | Jarrahi |
| 10,863,895 B2 | 12/2020 | Jarrahi |
| 11,112,305 B2 | 9/2021 | Jarrahi et al. |
| 11,231,318 B2 | 1/2022 | Jarrahi et al. |
| 2001/0011704 A1 | 8/2001 | Niwa et al. |
| 2003/0184328 A1 | 10/2003 | Lee et al. |
| 2004/0095147 A1 | 5/2004 | Cole |
| 2005/0236260 A1 | 10/2005 | Pasch et al. |
| 2006/0153262 A1 | 7/2006 | Barbieri et al. |
| 2007/0216422 A1 | 9/2007 | Sekiguchi |
| 2007/0278075 A1 | 12/2007 | Terano et al. |
| 2008/0001691 A1 | 1/2008 | Hong et al. |
| 2008/0277672 A1 | 11/2008 | Hovey et al. |
| 2009/0259102 A1 | 10/2009 | Koninckx et al. |
| 2009/0261362 A1 | 10/2009 | Ueda et al. |
| 2009/0273532 A1 | 11/2009 | Mendis et al. |
| 2010/0002739 A1 | 1/2010 | Hu et al. |
| 2010/0017922 A1 | 1/2010 | Shin et al. |
| 2010/0102256 A1 | 4/2010 | Andrew et al. |
| 2010/0277726 A1 | 11/2010 | Logan et al. |
| 2011/0028824 A1 | 2/2011 | Cole et al. |
| 2011/0074293 A1 | 3/2011 | Hagmann et al. |
| 2011/0080329 A1 | 4/2011 | Nagel |
| 2011/0141468 A1 | 6/2011 | Kukushkin et al. |
| 2011/0149368 A1 | 6/2011 | Kim et al. |
| 2011/0205528 A1* | 8/2011 | Ogawa ............... G01N 21/3581 356/51 |
| 2011/0215246 A1 | 9/2011 | Kajiki |
| 2012/0122259 A1 | 5/2012 | Tung et al. |
| 2012/0147907 A1 | 6/2012 | Kim et al. |
| 2012/0162747 A1 | 6/2012 | Kim et al. |
| 2012/0205767 A1 | 8/2012 | Bai et al. |
| 2012/0294549 A1 | 11/2012 | Doepke |
| 2013/0015375 A1 | 1/2013 | Avouris et al. |
| 2013/0161514 A1 | 6/2013 | Kukushkin et al. |
| 2013/0161541 A1 | 6/2013 | Kim et al. |
| 2013/0284929 A1 | 10/2013 | Ouchi |
| 2014/0103211 A1 | 4/2014 | Darcie et al. |
| 2014/0198973 A1 | 7/2014 | Zhang et al. |
| 2014/0346357 A1 | 11/2014 | Jarrahi et al. |
| 2015/0316475 A1 | 11/2015 | Rahman et al. |
| 2016/0064110 A1 | 3/2016 | Schmadel et al. |
| 2016/0116406 A1 | 4/2016 | Hunt et al. |
| 2016/0196943 A1 | 7/2016 | Jarrahi et al. |
| 2016/0305869 A1 | 10/2016 | Mann et al. |
| 2017/0123292 A1 | 5/2017 | Jarrahi |
| 2017/0131718 A1 | 5/2017 | Matsumura et al. |
| 2018/0058931 A1 | 3/2018 | Jarrahi et al. |
| 2019/0150719 A1 | 5/2019 | Jarrahi |
| 2020/0064259 A1 | 2/2020 | Jarrahi et al. |
| 2020/0264048 A1 | 8/2020 | Jarrahi et al. |
| 2023/0016600 A1 | 1/2023 | Jarrahi et al. |

FOREIGN PATENT DOCUMENTS

| | | |
|---|---|---|
| EP | 2807675 A1 | 12/2014 |
| EP | 3155702 A1 | 4/2017 |
| EP | 3302224 A2 | 4/2018 |
| EP | 3312590 A1 | 4/2018 |
| EP | 2807675 B1 | 9/2018 |
| EP | 3612812 A1 | 2/2020 |
| EP | 3302224 B1 | 10/2020 |
| EP | 3155702 B1 | 12/2020 |
| EP | 4038366 A1 | 8/2022 |
| EP | 4052458 A1 | 9/2022 |
| JP | 11056786 A | 3/1999 |
| JP | 2002511690 A | 4/2002 |
| JP | 2002511960 A | 4/2002 |
| JP | 2006216646 A | 8/2006 |
| JP | 2008122278 A | 5/2008 |
| JP | 2009105102 A | 5/2009 |
| JP | 2009531841 A | 9/2009 |
| JP | 2010510703 A | 4/2010 |
| JP | 2014112078 A | 6/2014 |
| JP | 2015513067 A | 4/2015 |
| JP | 6169614 B2 | 7/2017 |
| JP | 2017523601 A | 8/2017 |
| JP | 2018516667 A | 6/2018 |
| JP | 6860210 B2 | 3/2021 |
| JP | 6955337 B2 | 10/2021 |
| KR | 20080004467 A | 1/2008 |
| WO | 9846042 A1 | 10/1998 |
| WO | 2005019810 A2 | 3/2005 |
| WO | 2005019810 A3 | 5/2005 |
| WO | 2006030608 A1 | 3/2006 |
| WO | 2010011186 A1 | 1/2010 |
| WO | 2010021073 A1 | 2/2010 |
| WO | 2010044193 A1 | 4/2010 |
| WO | 2011028179 A1 | 3/2011 |
| WO | 2011118398 A1 | 9/2011 |
| WO | 2011129690 A2 | 10/2011 |
| WO | 2012057710 A1 | 5/2012 |
| WO | 2013112608 A1 | 8/2013 |
| WO | 2013116924 A1 | 8/2013 |
| WO | 2015021100 A1 | 2/2015 |
| WO | 2015192094 | 12/2015 |
| WO | 2016196309 A2 | 12/2016 |
| WO | 2016196309 A3 | 2/2017 |
| WO | 2018195429 A1 | 10/2018 |
| WO | 2019008570 A1 | 1/2019 |
| WO | 2021067635 A1 | 4/2021 |
| WO | 2021087459 A1 | 5/2021 |

OTHER PUBLICATIONS

Yardimci et al., "High power telecommunication-compatible photoconductive terahertz emitters based on plasmonic nano-antenna arrays," Applied Physics Letters, vol. 109, pp. 191103-1 to 191103-4. (Year: 2016).*
Berry et al., "Principles of Impedance Matching inPhotoconductive Antennas", Journal of Infrared, Millimeter, and Terahertz Waves, vol. 33, Sep. 27, 2012, pp. 1182-1189, doi: 10.1007/s10762-012-9937-3.
Berry et al., "Significant Performance Enhancement in Photoconductive Terahertz Optoelectronics by Incorporating Plasmonic Con-

(56) References Cited

OTHER PUBLICATIONS tact Electrodes", Nature Communication, vol. 4, No. 1622, Mar. 27, 2013, pp. 1-10, doi: 10.1038/ncomms.2638.
Berry et al., "Terahertz Generation Using Plasmonic Photoconductive Gratings", New Journal of Physics, vol. 14, No. 105029, Oct. 30, 2012, pp. 1-12, doi: 10.1088/1367-2630/14/10/105029.
Berry et al., "Ultrafast Photoconductors based on Plasmonic Gratings", IEEE, 2011, 2 Pgs.
Bioucas-Dias et al., "Two-Step Algorithms for Linear Inverse Problems with Non-Quadratic Regularization", IEEE, 2007, 4 Pgs.
Bjarnason et al., "ErAs: GaAs Photomixer with Two-Decade Tunability and 12 µW Peak Output Power", Applied Physics Letters, vol. 85, No. 18, Nov. 1, 2004, pp. 3983-3985, doi: 10.1063/1.1813635.
Born et al., "Monitoring Plant Drought Stress Response Using Terahertz Time-Domain Spectroscopy", Plant Physiology, vol. 164, Apr. 2014, pp. 1571-1577, doi: https://doi.org/10.1104/pp.113.233601.
Brown et al., "Characterization of a Planar Self-Complementary Square-Spiral Antenna in the THz Region", Microwave and Optical Technology Letters, vol. 48, No. 3, Mar. 2006, pp. 524-529, doi: 10.1002/mop.
Brown et al., "Coherent Millimeter-Wave Generation by Heterodyne Conversion in Low-Temperature-Grown GaAs Photoconductors", Journal of Applied Physics, vol. 73, No. 3, Feb. 1, 1993, pp. 1480-1484.
Cassel et al., "Aflatoxins: Hazards in Grain/Aflatoxicosis and Livestock", South Dakota State University, Fact Sheets, Paper 86, Oct. 1, 2001, 5 Pgs.
Castro-Camus et al., "Leaf Water Dynamics of *Arabidopsis thaliana* Monitored in-Vivo Using Terahertz Time-Domain Spectroscopy", Scientific Reports, vol. 3, No. 2910, Oct. 9, 2013, pp. 1-5, doi: 10.1038/srep02910.
Catrysse et al., "Guided Modes Supported by Plasmonic Films with a Periodic Arrangement of Subwavelength Slits", Applied Physics Letters, vol. 88, 2006, pp. 031101-1-031101-3, doi: 10.1063/1.2164905.
Chan et al., "Imaging with Terahertz Radiation", Reports on Progress in Physics, vol. 70, Jul. 12, 2007, pp. 1325-1379, doi: 10.1088/0034-4885/70/8/R02.
Chen et al., "A preliminary Study of Aflatoxin B1 Detection in Peanut Oil by Terahertz Time-Domain Spectroscopy", Transactions of the ASABE, vol. 57, No. 6, 2014, pp. 1793-1799, doi: 10.13031/trans.57.10725.
Chen et al., "Total Variation Deconvolution for Terahertz Pulsed Imaging", Inverse Problems in Science and Engineering, vol. 19, No. 2, Mar. 2011, pp. 223-232, doi: 10.1080/17415977.2010.550045.
Chimot et al., "Photomixing at 1.55 µm in Ion-Irradiated In0.53GA0.47As on InP", Optics Express, vol. 14, No. 5, Mar. 6, 2006, pp. 1856-1861.
Claudio et al., "Monitoring Drought Effects on Vegetation Water Content and Fluxes in Chaparral with the 970 nm Water Band Index", Remote Sensing of Environment, vol. 103, Aug. 15, 2006, pp. 304-311, doi: 10.1016/j.rse.2005.07.015.
Clothier et al., "Effects of THz Exposure on Human Primary Keratinocyte Differentiation and Viability", Journal of Biological Physics, vol. 29, 2003, pp. 179-185.
Cotrozzi et al., "Using Foliar Spectral Properties to Assess the Effects of Drought on Plant Water Potential", Tree Physiology, vol. 37, Sep. 19, 2017, pp. 1582-1591, doi: https://doi.org/10.1093/treephys/tpx106.
Danson et al., "High-Spectral Resolution Data for Determining Leaf Water Content", International Journal of Remote Sensing, vol. 13, No. 3, 1992, pp. 461-470, doi: https://doi.org/10.1080/01431169208904049.
Delmulle et al., "Development of an Immunoassay-Based Lateral Flow Dipstick for the Rapid Detection of Aflatoxin B1 in Pig Feed", Journal of Agricultural and Food Chemistry, vol. 53, Apr. 8, 2005, pp. 3364-3368, doi: https://doi.org/10.1021/jf0404804.

Dreyhaupt et al., "High-Intensity Terahertz Radiation from a Microstructured Large-Area Photoconductor", Applied Physics Letters, vol. 86, 2005, pp. 121114-1-121114-3, doi: 10.1063/1.1891304.
Federici et al., "THz imaging and sensing for security applications—explosives, weapons and drugs", Semiconductor Science and Technology, Jul. 1, 2005, vol. 20, No. 7, pp. S266-S280, XP020086549, ISSN: 0268-1242, DOI:10.1088/02681242/20/7/018.
Fitzgerald et al., "Catalogue of Human Tissue Optical Properties at Terahertz Frequencies", Journal of Biological Physics, vol. 29, 2003, pp. 123-128, doi: 10.1023/A:1024428406218.
Fitzgerald et al., "Nondestructive Analysis of Tablet Coating Thicknesses Using Terahertz Pulsed Imaging", Journal of Pharmaceutical Sciences, vol. 94, No. 1, Jan. 2005, pp. 177-183, doi: 10.1002/jps.20225.
Ge et al., "Quantitative Determination of Aflatoxin B1 Concentration in Acetonitrile by Chemometric Methods Using Terahertz Spectroscopy", Food Chemistry, vol. 209, 2016, pp. 286-292, doi: https://doi.org/10.1016/j.foodchem.2016.04.070.
Gente et al., "Contactless Water Status Measurements on Plants at 35 GHz", Journal of Infrared, Millimeter, and Terahertz Waves, vol. 36, 2015, pp. 312-317, doi: 10.1007/s10762-014-0127-3.
Gente et al., "Determination of Leaf Water Content from Terahertz Time-Domain Spectroscopic Data", Journal of Infrared, Millimeter, and Terahertz Waves, 2013, pp. 1-8.
Gente et al., "Outdoor Measurements of Leaf Water Content Using THz Quasi Time-Domain Spectroscopy", Journal of Infrared, Millimeter, and Terahertz Waves, vol. 39, Jul. 17, 2018, pp. 943-948, doi: https://doi.org/10.1007/s10762-018-0520-4.
Gowen et al., "Terahertz Time Domain Spectroscopy and Imaging: Emerging Techniques for Food Process Monitoring and Quality Control", Trends in Food Science & Technology, vol. 25, 2012, pp. 40-46, doi: 10.1016/j.tifs.2011.12.006.
Gregory et al., "Optimization of Photomixers and Antennas for Continuous-Wave Terahertz Emission", IEEE Journal of Quantum Electronics, vol. 41, No. 5, May 2005, pp. 717-728, doi: 10.1109/JQE.2005.844471.
Grischkowsky et al., "Far-Infrared Time-Domain Spectroscopy with Terahertz Beams of Dielectrics and Semiconductors", Journal of the Optical Society of America B, vol. 7, No. 10, Oct. 1990, pp. 2006-2015, doi: https://doi.org/10.1364/JOSAB.7.002006.
Gu et al., "Detection of Terahertz Radiation from Longitudinal Optical Phonon-Plasmon Coupling Modes in InSb Film Using an Ultrabroadband Photoconductive Antenna", Applied Physics Letters, vol. 77, No. 12, Sep. 18, 2000, pp. 1798-1800.
Hadjiloucas et al., "Measurements of Leaf Water Content Using Terahertz Radiation", IEEE Transactions on Microwave Theory and Techniques, vol. 47, No. 2, Feb. 1999, pp. 142-149, doi: 10.1109/22.744288.
Heshmat et al., "Nanoplasmonic Terahertz Photoconductive Switch on GaAs", Nano Letters, vol. 12, Nov. 21, 2012, pp. 6255-6259, doi: dx.doi.org/10.1021/nl303314a.
Howell, "EV Everywhere Grand Challenge—Battery Status and Cost Reduction Prospects", U.S. Department of Energy, Jul. 26, 2012, Retrieved from the Internet <https://www1.eere.energy.gov/vehiclesandfuels/pdfs/ev_everywhere/5_howell_b.pdf>, 15 Pgs.
Hsieh et al., "Analysis of Periodic metallic nano-slits for efficient interaction of terahertz and optical waves at nano-scale dimensions", Journal of Applied Physics, vol. 109, 2011, pp. 084326-1-084326-5.
Hsieh et al., "Electrochemical-Acoustic Time of Flight: in Operando Correlation of Physical Dynamics with Battery Charge and Health", Energy & Environmental Science, vol. 8, 2015, pp. 1569-1577, doi: 10.1039/c5ee00111k.
Hu et al., "Imaging with Terahertz Waves", Optics Letters, vol. 20, No. 16, Aug. 15, 1995, pp. 1716-1718, doi: https://doi.org/10.1364/OL.20.001716.
Huang et al., "Tissue Characterization Using Terahertz Pulsed Imaging in Reflection Geometry", Physics in Medicine and Biology, vol. 54, 2009, pp. 149-160, doi: 10.1088/0031-9155/54/1/010.
Humphreys et al., "Medical Applications of Terahertz Imaging: A Review of Current Technology and Potential Applications in Bio-

(56) References Cited

OTHER PUBLICATIONS medical Engineering", Proceedings of the 26th Annual International Conference of the IEEE EMBS San Francisco, CA, USA Sep. 1-5, 2004, pp. 1302-1305.
Hunt, Jr. et al., "Detection of Changes in Leaf Water Content Using Near- and Middle-Infrared Reflectances", Remote Sensing of Environment, vol. 30, 1989, pp. 43-54, doi: https://doi.org/10.1016/0034-4257(89)90046-1.
Hunt, Jr. et al., "Measurement of Leaf Relative Water Content by Infrared Reflectance", Remote Sensing of Environment, vol. 22, pp. 1987, 429-435.
Huo et al., "Planar Log-Periodic Antennas on Extended Hemispherical Silicon Lenses for Millimeter/Submillimeter Wave Detection Applications", International Journal of Infrared and Millimeter Waves, vol. 23, No. 6, Jun. 2002, pp. 819-839.
Jacques, "Optical Properties of Biological Tissues: A Review", Physics in Medicine and Biology, vol. 58, May 10, 2013, pp. R37-R61, doi: 10.1088/0031-9155/58/11/R37.
Jarrahi, "Advanced Photoconductive Terahertz Optoelectronics Based on Nano-Antennas and Nano-Plasmonic Light Concentrators", IEEE Transactions on Terahertz Science and Technology, vol. 5, No. 3, May 2015, pp. 391-397, doi: 10.1109/TTHZ.2015.2406117.
Jepsen et al., "Terahertz Spectroscopy and Imaging—Modern Techniques and Applications", Laser & Photonics Reviews, vol. 5, No. 1, 2011, pp. 124-166, doi: 10.1002/lpor.201000011.
Jördens et al., "Evaluation of Leaf Water Status by Means of Permittivity at Terahertz Frequencies", Journal of Biological Physics, vol. 35, Jun. 11, 2009, pp. 255-264, doi: 10.1007/s10867-009-9161-0.
Just et al., "A Method to Quantify Coating Thickness and Porosity of Electrodes for Lithium-Ion-Batteries", Measurement, vol. 89, 2016, pp. 312-315.
Kindt et al., "Far-Infrared Dielectric Properties of Polar Liquids Probed by Femtosecond Terahertz Pulse Spectroscopy", Journal of Physical Chemistry, vol. 100, 1996, pp. 10373-10379.
Knipling, "Physical and Physiological Basis for the Reflectance of Visible and Near-Infrared Radiation from Vegetation", Remote Sensing of Environment, vol. 1, 1970, pp. 155-159, doi: https://doi.org/10.1016/S0034-4257(70)80021-9.
Kokkonen et al., "Determination of Selected Mycotoxins in Mould Cheeses with Liquid Chromatography Coupled to Tandem with Mass Spectrometry", Food Additives and Contaminants, vol. 22, No. 5, May 2005, pp. 449-456, doi: 10.1080/02652030500089861.
Krimi et al., "Highly Accurate Thickness Measurement of Multi-Layered Automotive Paints Using Terahertz Technology", Applied Physics Letters, vol. 109, Jul. 12, 2016, pp. 021105-1-021105-4.
Krishnamachari et al., "Hepatitis Due to Aflatoxicosis, An Outbreak in Western India", The Lancet, May 10, 1975, pp. 1061-1063, doi: 10.1016/S0140-6736(75)91829-2.
Kubiske et al., "Pressure-Volume Relationships in Non-Rehydrated Tissue at Various Water Deficits", Plant, Cell & Environment, vol. 13, May 17, 1990, pp. 995-1000.
Lecun et al., "Convolutional Networks for Images, Speech, and Time-Series", The Handbook of Brain Theory and Neural Networks, 1998, 14 Pgs.
Li et al., "A Polarization-Insensitive Plasmonic Photoconductive Terahertz Emitter", AIP Advances, vol. 7, Nov. 16, 2017, pp. 115113-1-15513-6, doi: https://doi.org/10.1063/1.5006273.
Li et al., "Measurements and Analysis of Water Content in Winter Wheat Leaf Based on Terahertz Spectroscopy", International Journal of Agricultural and Biological Engineering, vol. 11, No. 3, May 2018, pp. 178-182, doi: 10.25165/j.ijabe.20181103.3520.
Li et al., "Monitoring Soybean Leaf Water Status using Terahertz Spectroscopy", 2018 43rd International Conference on Infrared, Millimeter, and Terahertz Waves(IRMMW-THZ), IEEE, Sep. 9, 2018, p. 1, XP033430718, DOI: 10.1109/IRMMW-THZ.2018.8510251.
Liu et al., "Coherent Detection of Multiband Terahertz Radiation Using a Surface Plasmon-Polariton Based Photoconductive Antenna", IEEE Transactions on Terahertz Science and Technology, vol. 1, No. 2, Nov. 2011, pp. 412-415, doi: 10.1109/TTHZ/2011.2165241.
Loata et al., "Radiation Field Screening in Photoconductive Antennae Studied via Pulsed Terahertz Emission Spectroscopy", Applied Physics Letters, vol. 91, 2007, pp. 232506-1-232506-3, doi: 10.1063/1.2823590.
Malone et al., "Determination of Aflatoxins in Grains and Raw Peanuts by a Rapid Procedure with Fluorometric Analysis", Journal of AOAC International, vol. 83, No. 1, 2000, pp. 95-98.
Mangeney et al., "Continuous Wave Terahertz Generation up to 2 THz by Photomixing on Ion-Irradiated in0.53GA0.47As at 1.55 µm Wavelengths", Applied Physics Letters, vol. 91, Dec. 10, 2007, pp. 241102-1-241102-3, doi: 10.1063/1.2817607.
Michael et al., "Large-Area Traveling-Wave Photonic Mixers for Increased Continuous Terahertz Power", Applied Physics Letters, vol. 86, Mar. 11, 2005, pp. 111120-1-111120-3, doi: 10.1063/1.1884262.
Middendorf et al., "THz Generation Using Extrinsic Photoconductivity at 1550 nm", Optics Express, vol. 20, No. 15, Jul. 16, 2012, pp. 16504-16509.
Mittleman et al., "Gas Sensing Using Terahertz Time-Domain Spectroscopy", Applied Physics B Lasers and Optics, vol. 67, Feb. 25, 1998, pp. 379-390.
Mittleman et al., "T-Ray Imaging", IEEE Journal of Selected Topics in Quantum Electronics, vol. 2, No. 3, Sep. 1996, pp. 679-689, doi: 10.1109/2944.571768.
Mohanty et al., "Non-Destructive Evaluation of Slot-Die-Coated Lithium Secondary Battery Electrodes by in-line Laser Caliper and IR Thermography Methods", Analytical Methods, vol. 6, 2014, pp. 674-683, doi: 10.1039/C3AY41140K.
Momen et al., "Interacting Effects of Leaf Water Potential and Biomass on Vegetation Optical Depth", Journal of Geophysical Research: Biogeosciences, vol. 122, Nov. 23, 2017, pp. 3031-3046, doi: https://doi.org/10.1002/2017JG004145.
Nagatsuma et al., "Terahertz Imaging Based on Optical Coherence Tomography", Photonics Research, vol. 2, No. 4, Aug. 2014, pp. B64-B69, doi: https://doi.org/10.1364/PRJ.2.000B64.
Ng, "Sparse Autoencoder", CS294A Lecture notes, 2011, 1-19.
Okyay et al., "High-Efficiency Metal-Semiconductor-Metal Photodetectors on Heteroepitaxially Grown Ge on Si", Optics Letters, vol. 31, No. 17, Sep. 1, 2006, pp. 2565-2567, doi: 10.1364/OL.31.002565.
Ollinger, "Tansley review: Sources of Variability in Canopy Reflectance and the Convergent Properties of Plants", New Phytologist, vol. 189, 2011, pp. 375-394, doi: 10.1111/j.1469-8137.2010.03536.x.
European Examination Report Corresponding to EP Application No. 13741491.8, Dated Oct. 21, 2015, 5 Pages.
Extended European Search Report for European Application No. 15807544.0, Search completed Jun. 12, 2018, and Mailed Jun. 20, 2018, 8 Pgs.
Extended European Search Report for European Application No. 16804130.9, Search completed Jan. 16, 2019, Mailed Jan. 25, 2019, 6 Pgs.
Extended European Search Report for European Application No. 18787213.0, Search completed Nov. 30, 2020, Mailed Dec. 9, 2020, 7 Pgs.
Extended European Search Report for European Application No. 20883093.5, Search completed Oct. 13, 2023, Mailed Oct. 26, 2023, 25 Pgs.
https://www.advantest.com/cs/groups/public/documents/document/zhzw/mdex/~edisp/advp011862.pdf.
International Preliminary Report on Patentability for International Application PCT/US2013/022776, Report issued Jul. 29, 2014, Mailed Aug. 7, 2014, 8 Pgs.
International Preliminary Report on Patentability for International Application PCT/US2014/049866, Report issued Feb. 9, 2016, Mailed Feb. 18, 2016, 8 Pgs.
International Preliminary Report on Patentability for International Application PCT/US2015/035685, Report issued Dec. 15, 2016, Mailed Dec. 22, 2016, 7 Pgs.
International Preliminary Report on Patentability for International Application PCT/US2016/034704, Report issued Nov. 28, 2017, Mailed Dec. 7, 2017, 10 Pgs.

(56) References Cited

OTHER PUBLICATIONS

International Preliminary Report on Patentability for International Application PCT/US2018/028579, Report issued Oct. 22, 2019, Mailed Oct. 31, 2019, 8 Pgs.
International Preliminary Report on Patentability for International Application PCT/US2020/053860, Report issued Apr. 5, 2022, Mailed on Apr. 14, 2022, 8 Pgs.
International Preliminary Report on Patentability for International Application PCT/US2020/058549, Report issued May 3, 2022, Mailed May 12, 2022, 12 Pgs.
International Search Report and Written Opinion for International Application No. PCT/US2013/022776, Search completed May 15, 2013, Mailed May 16, 2013, 9 Pgs.
International Search Report and Written Opinion for International Application No. PCT/US2014/049866, Search completed Nov. 19, 2014, Mailed Nov. 20, 2014, 9 Pgs.
International Search Report and Written Opinion for International Application No. PCT/US2016/034704, Search completed Dec. 26, 2016, Mailed Dec. 26, 2016, 11 Pgs.
International Search Report and Written Opinion for International Application No. PCT/US2018/028579, Search completed Jul. 5, 2018, Mailed Jul. 20, 2018, 11 Pgs.
International Search Report and Written Opinion for International Application No. PCT/US2020/053860, Search completed Nov. 30, 2020, Mailed Jan. 6, 2021, 14 Pgs.
International Search Report and Written Opinion for International Application No. PCT/US2020/058549, Search completed Feb. 16, 2021, Mailed Mar. 23, 2021, 18 Pgs.
International Search Report and Written Opinion for International Application PCT/US2015/035685, Report Completed Aug. 27, 2015, Mailed Aug. 27, 2015, 8 Pgs.
Partial Supplementary European Search Report for European Application No. 20871922.9, Search completed Sep. 28, 2023, Mailed Oct. 11, 2023, 16 pgs.
Supplementary European Search Report for European Application No. 13741491.8, Search completed Sep. 28, 2015, Mailed Oct. 12, 2015, 6 Pgs.
Ajito et al., "THz Chemical Imaging for Biological Applications", IEEE Transactions on Terahertz Science and Technology, vol. 1, No. 1, Sep. 2011, pp. 293-300, doi: 10.1109/TTHZ.2011.2159562.
Alshannaq et al., "Controlling Aflatoxin Contamination and Propagation of Aspergillus Flavus by a Soy-Fermenting Aspergillus Oryzae Strain", Scientific Reports, vol. 8, No. 16871, Nov. 15, 2018, pp. 1-14, doi: 10.1038/s41598-018-35246-1.
Anastasi et al., "Terahertz NDE for Metallic Surface Roughness Evaluation", SPIE 11th Annual International Symposium on Nondestructive Evaluation for Health Monitoring and Diagnostics, Jun. 19, 2006, pp. 57-62.
Anastasi et al., "Terahertz NDE for Under Paint Corrosion Detection and Evaluation", Annual Review of Progress in Quantitative Nondestructive Evaluation, Jul. 21-Aug. 4, 2005, pp. 49-56.
Arbab et al., "Terahertz Spectroscopy for the Assessment of Burn Injuries in Vivo", Journal of Biomedical Optics, vol. 18, No. 7, Jul. 2013, pp. 077004-1-077004-7, doi: 10.1117/1.JBO.18.7.077004.
Ashworth et al., "Terahertz Pulsed Spectroscopy of Freshly Excised Human Breast Cancer", Optics Express, vol. 17, No. 15, Jul. 20, 2009, pp. 12444-12454, doi: https://doi.org/10.1364/OE.17.012444.
Asner et al., "Progressive Forest Canopy Water Loss during the 2012-2015 California Drought", Proceedings of the National Academy of Sciences, Dec. 28, 2015, pp. E249-E255, doi: www.pnas.org/cgi/doi/10.1073/pnas.1523397113.
Baek et al., "Detection of Melamine in Foods Using Terahertz Time-Domain Spectroscopy", Journal of Agriculture and Food Chemistry, vol. 62, Jun. 2, 2014, pp. 5403-5407, doi: dx.doi.org/10.1021/jf501170z.
Baker et al., "Self-Triggered Asynchronous Optical Sampling Terahertz Spectroscopy Using a Bidirectional Mode-locked Fiber Laser", Scientific Reports, vol. 8, No. 14802, Oct. 4, 2018, pp. 1-8, doi: 10.1038/s41598-018-33152-0.
Baldacci et al., "Non-Invasive Absolute Measurement of Leaf Water Content Using Terahertz Quantum Cascade Lasers", Plant Methods, vol. 13, No. 51, Jun. 17, 2017, pp. 1-7, doi: 10.1186/s13007-017-0197-z.
Bartlett et al., "The Correlations and Sequence of Plant Stomatal, Hydraulic, and Wilting Responses to Drought", The Proceedings of the National Academy of Sciences, vol. 113, No. 46, Nov. 15, 2016, pp. 13098-13103, doi: www.pnas.org/cgi/doi/10.1073/pnas.1604088113.
Bartlett et al., "The Determinants of Leaf Turgor Loss Point and Prediction of Drought Tolerance of Species and Biomes: A Global Meta-Analysis", Ecology Letters, vol. 15, 2012, pp. 393-405, doi: 10.1111/j.1461-0248.2012.01751.x.
Beck et al., "Impulsive Terahertz Radiation with High Electric Fields from an Amplifier-Driven Large-Area Photoconductive Antenna", Optics Express, vol. 18, No. 9, Apr. 26, 2010, pp. 9251-9257, doi: https://doi.org/10.1364/OE.18.009251.
Bennett et al., "Aflatoxins: Background, Toxicology, and Molecular Biology", Foodborne Diseases, Humana Press Inc., 2007, pp. 355-373, doi: 10.1007/978-1-59745-501-5_13.
Berry et al., "Design, Fabrication, and Experimental Characterization of Plasmonic Photoconductive Terahertz Emitters", Journal of Visualized Experiments, vol. 77, No. e50517, Jul. 2013, pp. 1-8, doi: 10.3791/50517.
Berry et al., "Generation of High Power Pulsed Terahertz Radiation Using a Plasmonic Photoconductive Emitter Array with Logarithmic Spiral Antennas", Applied Physics Letters, vol. 104, 2014, pp. 081122-1-081122-4, doi: http://dx.doi.org/10.1063/1.4866807.
Berry et al., "High Power Terahertz Generation Using 1550 nm Plasmonic Photomixers", Applied Physics Letters, vol. 105, Jul. 10, 2014, pp. 011121-1-011121-4, doi: http://dx.doi.org/10.1063/1.4890102.
Berry et al., "Nanoscale Contact Electrodes for Significant Radiation Power Enhancement in Photoconductive Terahertz Emitters", IEEE, 2013, 4 Pgs.
Berry et al., "Plasmonic Photomixers for Increased Terahertz Radiation Powers At 1550 nm Optical Pump Wavelength", IEEE, 2014, 2 Pgs.
Berry et al., "Plasmonically-Enhanced Localization of Light into Photoconductive Antennas", IEEE, 2010, 2 Pgs.
Berry et al., "Plasmonics Enhanced Photomixing for Generating Quasi-Continuous-Wave Frequency-Tunable Terahertz Radiation", Optics Letters, Aug. 1, 2014, vol. 39, No. 15, pp. 4522-4524.
Park et al., "Enhancement of Terahertz Pulse Emission by Optical Nanoantenna", ACS Nano, vol. 6, No. 3, Feb. 17, 2012, pp. 2026-2031, doi: 10.1021/nn204542x.
Park et al., "Terahertz Photoconductive Antenna with Metal Nanoislands", Optics Express, vol. 20, No. 23, Nov. 5, 2012, pp. 25530-25535.
Parrott et al., "Terahertz spectroscopy: Its future role in medical diagnoses", Journal of Molecular Structure, Dec. 14, 2011, vol. 1006, Issues 1-3, pp. 66-76, doi.org/10.1016/j.molstruc.2011.05.048.
Pearson et al., "Detecting Aflatoxin in Single Corn Kernels by Transmittance and Reflectance Spectroscopy", Transactions of the ASAE, vol. 44, No. 5, 2001, pp. 1247-1254, doi: 10.13031/2013.6418.
Peñuelas et al., "Reflectance Indices Indicative of Changes in Water and Pigment Contents of Peanut and Wheat Leaves", Photosynthetica, vol. 36, No. 3, 1999, pp. 355-360, doi: 10.1023/A:1007033503276.
Peñuelas et al., "The Reflectance at the 950-970 nm Region as an Indicator of Plant Water Status", International Journal of Remote Sensing, vol. 14, No. 10, 1993, pp. 1887-1905.
Peter et al., "Coherent Terahertz Detection with a Large-Area Photoconductive Antenna", Applied Physics Letters, vol. 91, No. 081109, Aug. 21, 2007, pp. 40-42, doi: 10.1063/1.2772783.
Peytavit et al., "Continuous Terahertz-Wave Generation Using a Monolithically Integrated Horn Antenna", Applied Physics Letters, vol. 93, Sep. 16, 2008, pp. 111108-1-111108-3, doi: 10.1063/1.2983741.

(56) References Cited

OTHER PUBLICATIONS

Peytavit et al., "Milliwatt-Level Output Power in the Sub-Terahertz Range Generated by Photomixing in a GaAs Photoconductor", Applied Physics Letters, vol. 99, 2011, pp. 223508-1-223508-3, doi: 10.1063/1.3664635.

Pickwell-MacPherson, "Practical Considerations for in Vivo THz Imaging", Terahertz Science and Technology, vol. 3, No. 4, Dec. 2010, pp. 163-171, doi: 10.11906/TST.163-171.2010.12.16.

Pietsch et al., "X-Ray Tomography for Lithium Ion Battery Research: A Practical Guide", Annual Review of Materials Research, vol. 47, 2017, pp. 451-479.

Preu et al., "1550 nm ErAs: In(Al)GaAs Large Area Photoconductive Emitters", Applied Physics Letters, vol. 101, 2012, pp. 101105-1-101105-4, doi: https://doi.org/10.1063/1.4750244.

Preu et al., "Tunable, continuous-wave Terahertz photomixer sources and applications", Journal of Applied Physics, vol. 109, 2011, published online Mar. 22, 2011, pp. 016301-1-061301-56, doi: 10.1063/1.3552291.

Pupeza et al., "Highly Accurate Optical Material Parameter Determination with THz Time-Domain Spectroscopy", Optics Express, vol. 15, No. 7, Apr. 2, 2007, pp. 4335-4350, doi: 10.1364/oe.15.004335.

Qu et al., "Function of Terahertz Spectra in Monitoring the Decomposing Process of Biological Macromolecules and in Investigating the Causes of Photoinhibition", Science China Life Sciences, vol. 60, No. 3, Mar. 2017, pp. 307-312, doi: 10.1007/s11427-016-0057-9.

Qu et al., "Review of Theoretical Methods and Research Aspects for Detecting Leaf Water Content Using Terahertz Spectroscopy and Imaging", International Journal of Agricultural and Biological Engineering, vol. 11, No. 5, Sep. 2018, pp. 27-34, doi: 10.25165/j.ijabe.20181105.3952.

Rao et al., "Satellite-Based Vegetation Optical Depth as an Indicator of Drought-Driven Tree Mortality", Remote Sensing of Environment, vol. 227, Apr. 13, 2019, pp. 125-136, doi: 10.1016/j.rse.2019.03.026.

Rapaport et al., "Combining Leaf Physiology, Hyperspectral Imaging and Partial Least Squares-Regression (PLS-R) for Grapevine Water Status Assessment", ISPRS Journal of Photogrammetry and Remote Sensing, vol. 109, Sep. 27, 2015, pp. 88-97, doi: https://doi.org/10.1016/j.isprsjprs.2015.09.003.

Rapaport et al., "The Potential of the Spectral 'Water Balance Index' (WABI) for Crop Irrigation Scheduling", New Phytologist, 2017, pp. 1-16, doi: 10.1111/nph.14718.

Ren et al., "State-of-the-art in terahertz sensing for food and water security—A comprehensive review", Trends in Food Science & Technology, Jun. 8, 2005 (Jun. 8, 2005), vol. 85, pp. 241-251, XP085605185, ISSN: 0924-2244, DOI: 10.1016/J.TIFS.2019.01.019.

Roehle et al., "Next Generation 1.5 μm Terahertz Antennas: Mesa-Structuring of InGaAs/InAlAs Photoconductive Layers", Optics Express, vol. 18, No. 3, Feb. 1, 2010, pp. 2296-2301.

Ronne et al., "THz Spectroscopy of Liquid H2O and D2O", Physical Review Letters, vol. 82, No. 14, Apr. 5, 1999, pp. 2888-2891, doi: 10.1103/PhysRevLett.82.2888.

Sack et al., "ABA Accumulation in Dehydrating Leaves is Associated with Decline in Cell Volume, Not Turgor Pressure", Plant Physiology, Jan. 1, 2018, vol. 176, No. 1, pp. 489-495, XP055930242, doi: www.plantphysiol.org/cgi/doi/10.1104/pp.17.01097.

Sack et al., "Leaf Pressure-Volume Curve Parameters", Wiki, 2017, pp. 1-2.

Sancho-Knapik et al., "Microwave L-Band (1730 MHz) Accurately Estimates the Relative Water Content in Poplar Leaves. A Comparison with a Near Infrared Water Index (R1300/R1450)", Agricultural and Forest Meteorology, vol. 151, Jul. 27, 2011, pp. 827-832, doi: 10.1016/j.agrformet.2011.01.016.

Santesteban et al., "Terahertz time Domain Spectroscopy Allows Contactless Monitoring of Grapevine Water Status", Frontiers in Plant Science, vol. 6, No. 404, Jun. 2015, pp. 1-9, doi: 10.3389/fpls.2015.00404.

Schindelin et al., "Fiji—An Open-Source Platform for Biological-Image Analysis", Nature Methods, vol. 9, No. 7, Dec. 7, 2013, pp. 1-15, doi: 10.1038/nmeth.2019.

Schmale, III et al., "Mycotoxins in Crops: A Threat to Human and Domestic Animal Health", The Plant Health Instructor, 2009, 19 Pgs, doi: 10.1094/PHI-I-2009-0715-01.

Scoffoni et al., "Dynamics of Leaf Hydraulic Conductance with Water Status: Quantification and Analysis of Species Differences Under Steady State", Journal of Experimental Botany, vol. 63, No. 2, 2012, pp. 643-658, doi: 10.1093/jxb/err270.

Scoffoni et al., "Leaf Shrinkage with Dehydration: Coordination with Hydraulic Vulnerability and Drought Tolerance", Plant Physiology, vol. 164, Apr. 2014, pp. 1772-1788, doi: ww.plantphysiol.org/doi/10.1104/pp.113.221424.

Shen et al., "Properties of a One-Dimensional Metallophotonic Crystal", Physical Review B, vol. 70, 2004, pp. 035101-1-038101-8, doi: 10.1103/PhysRevB.70.035101.

Shibuya et al., "Enhancement of THz Photomixing Efficiency by Using a Pulse-Modulated Multimode Laser Diode", IEEE, 2007, 2 Pgs.

Sims et al., "Relationships Between Leaf Pigment Content and Spectral Reflectance Across a Wide Range of Species, Leaf Structures and Developmental Stages", Remote Sensing of Environment, vol. 81, Jan. 12, 2002, pp. 337-354, doi: https://doi.org/10.1016/S0034-4257(02)00010-X.

Singh et al., "Terahertz 3D Water Distribution in Plant Leaves", 44th International Conference on Infrared, Millimeter, and Terahertz Waves (IRMMW-THZ), IEEE, Sep. 1, 2019, pp. 1-2, XP033636539, DOI: 10.1109/IRMMW-THZ.2019.8873718.

Song et al., "Temporal and Spatial Variability of Water Status in Plant Leaves by Terahertz Imaging", IEEE Transactions on Terahertz Science and Technology, IEEE, Sep. 1, 2018, vol. 8, No. 5, pp. 520-527, XP011689856, DOI: 10.1109/TTHZ.2018.2851922.

Stevens et al., "Global Health Risks: Progress and Challenges", Bulletin of the World Health Organization, vol. 87, 2009, 3 Pgs, doi: 10.2471/BLT.09.070565.

Sukhotin et al., "Photomixing and Photoconductor Measurements on ErAs/InGaAs at 1.55 μm", Applied Physics Letters, vol. 82, No. 18, May 5, 2003, pp. 3116-3118, doi: 10.1063/1.1567459.

Sun et al., "A Promising Diagnostic Method: Terahertz Pulsed Imaging and Spectroscopy", World Journal of Radiology, vol. 3, No. 3, Mar. 28, 2011, pp. 55-65, doi: 10.4329/wjr.v3.i3.55.

Sun et al., "Room Temperature GaN/AlGaN Self-Mixing Terahertz Detector Enhanced by Resonant Antennas", Applied Physics Letters, vol. 98, No. 25, Jun. 20, 2011, pp. 252103-1-252103-3, doi: 10.1063/1.3601489.

Suzuki et al., "Fe-Implanted InGaAs Terahertz Emitters for 1.56 μm Wavelength Excitation", Applied Physics Letters, vol. 86, Jan. 27, 2005, pp. 051104-1-051104-3, doi: 10.1063/1.1861495.

Takayanagi et al., "High-Resolution Time-of-Flight Terahertz Tomography Using a Femtosecond Fiber Laser", Optics Express, vol. 17, No. 9, Apr. 27, 2009, pp. 7549-7555, doi: 10.1364/OE.17.007533.

Takazato et al., "Detection of Terahertz Waves Using Low-Temperature-Grown InGaAs with 1.56 μm Pulse Excitation", Applied Physics Letters, vol. 90, Mar. 9, 2007, pp. 101119-1-1011119-3, doi: 10.1063/1.2712503.

Tani et al., "Detection of Terahertz Radiation with Low-Temperature-Grown GaAs-Based Photoconductive Antenna Using 1.55 μm Probe", Applied Physics Letters, vol. 77, No. 9, Aug. 28, 2000, pp. 1396-1398, doi: https://doi.org/10.1063/1.1289914.

Tanigawa et al., "Enhanced Responsivity in a Novel AlGaN/GaN Plasmon-Resonant Terahertz Detector Using Gate-Dipole Antenna with Parasitic Elements", IEEE, 2010, pp. 167-168.

Taylor et al., "Resonant-Optical-Cavity Photoconductive Switch with 0.5% Conversion Efficiency and 1.0 W Peak Power", Optics Letters, vol. 31, No. 11, Jun. 1, 2006, pp. 1729-1731.

Thrane et al., "THz Reflection Spectroscopy of Liquid Water", Chemical Physics Letters, vol. 240, Jun. 30, 1995, pp. 330-333.

Tonouchi, "Cutting-Edge Terahertz Technology", Nature Photonics, vol. 1, Feb. 2007, pp. 97-105, doi: 10.1038/nphoton.2007.3.

Trueba et al., "Thresholds for Leaf Damage Due to Dehydration: Declines of Hydraulic Function, Stomatal Conductance and Cellular

(56) References Cited

OTHER PUBLICATIONS

Integrity Precede those for Photochemistry", New Phytologist, vol. 223, Feb. 18, 2019, pp. 134-149, doi: 10.1111/nph.15779.
Tsuda et al., "Application of Plasmon-Resonant Microchip Emitters to Broadband Terahertz Spectroscopic Measurement", Journal of the Optical Society of America B, vol. 26, No. 9, Sep. 2009, p. A52-A57.
Tucker, "Remote Sensing of Leaf Water Content in the Near Infrared", Remote Sensing of Environment, vol. 10, 1980, pp. 23-32, doi: https://doi.org/10.1016/0034-4257(80)90096-6.
Turan et al., "Impact of the Metal Adhesion Layer on the Radiation Power of Plasmonic Photoconductive Terahertz Sources", Journal of Infrared, Millimeter, and Terahertz Waves, vol. 38, Aug. 28, 2017, pp. 1448-1456, doi: 10.1007/s10762-017-0431-9.
Ueno et al., "Quantitative Measurements of Amino Acids by Terahertz Time-Domain Transmission Spectroscopy", Analytical Chemistry, vol. 78, No. 15, Aug. 1, 2006, pp. 5424-5428, doi: https://doi.org/10.1021/ac060520y.
Unknown Author, "Guidance for Industry: Action levels for Poisonous or Deleterious Substances in Human food and Animal Feed", Food and Drug Administration, Aug. 2000, 18 Pgs.
Unknown Author, "IARC Monographs on the Evaluation of Carcinogenic Risks to Humans: Re-Evaluation of Some Organic Chemicals, Hydrazine and Hydrogen Peroxide", World Health Organization, International Agency for Research on Cancer, vol. 71, 1999, 1597 Pgs., Presented in 12 parts.
Unknown Author, "Mycotoxins: Risks in Plant, Animal, and Human Systems", Council for Agricultural Science and Technology, Task Force Report, No. 139, Jan. 2003, 217 Pgs., Presented in 3 parts.
Unknown Author, "Xilinx and Altera FPGA Integration Modules", Opal Kelly, Apr. 2023, Retrieved from the Internet <https://www.opalkelly.com/>, 7 Pgs.
Utkin et al., "Adaptive Sliding Mode Control with Application to Super-Twist Algorithm: Equivalent Control Method", Automatica, vol. 49, 2013, pp. 39-47.
Wacoo et al., "Methods for Detection of Aflatoxins in Agricultural Food Crops", Journal of Applied Chemistry, vol. 2014, No. 706291, Nov. 13, 2014, pp. 1-15. doi: https://dx.doi.org/10.1155/2014/706291.
Wallace et al., "Terahertz Pulsed Imaging and Spectroscopy for Biomedical and Pharmaceutical Applications", Faraday Discussions, vol. 126, 2004, pp. 255-263, doi: 10.1039/b309357n.
Wallace et al., "Three-Dimensional Imaging of Optically Opaque Materials Using Nonionizing Terahertz Radiation", Journal of the Optical Society of America A, vol. 25, No. 12, Dec. 2008, pp. 3120-3133, doi: https://doi.org/10.1364/JOSAA.25.003120.
Wang et al., "Noise Analysis of Photoconductive Terahertz Detectors", Journal of Infrared, Millimeter, and Terahertz Waves, vol. 34, Jul. 11, 2013, pp. 519-528, doi: 10.1007/s10762-013-9995-1.
Wang et al., "Plasmonic Photoconductive Detectors for Enhanced Terahertz Detection Sensitivity", Optics Express, 2013, 7 Pgs.
Wang et al., "Terahertz Imaging Applications in Agriculture and Food Engineering: A Review", Transactions of the ASABE, vol. 61, No. 2, 2018, pp. 411-424, doi: https://doi.org/10.13031/trans.12201.
Williams et al., "Human Aflatoxicosis in Developing Countries: A Review of Toxicology, Exposure, Potential Health Consequences, and Interventions", The American Journal of Clinical Nutrition, vol. 80, 2004, pp. 1106-1122, doi: 10.1093/ajcn/80.5.1106.
Xing et al., "Nondestructive Examination of Polymethacrylimide Composite Structures with Terahertz Time-Domain Spectroscopy", Polymer Testing, Nov. 22, 2016, vol. 57, pp. 141-148, XP029857453, DOI: 10.1016/J.POLYMERTESTING.2016.11.022.
Yang et al., "7.5% Optical-to-Terahertz Conversion Efficiency Offered by Photoconductive Emitters with Three-Dimensional Plasmonic Contact Electrodes", IEEE Transactions on Terahertz Science and Technology, vol. 4, No. 5, Sep. 2014, pp. 575-581, doi: 10.1109/TTHZ.2014.2342505.
Yang et al., "Enhanced Light-Matter Interaction at Nanoscale by Utilizing High-Aspect-Ratio Metallic Gratings", Optics Letters, vol. 38, No. 18, Sep. 15, 2013, pp. 3677-3679, doi: http://dx.doi.org/10.1364/OL.38.003677.
Yang et al., "Frequency-Tunable Continuous-Wave Terahertz Sources Based on GaAs Plasmonic Photomixers", Applied Physics Letters, vol. 107, 2015, pp. 131111-1-131111-4, doi: http://dx.doi.org/10.1063/1.4932114.
Yang et al., "Measurement of the Transmission of the Atmosphere from 0.2 to 2 THz", Optic Express, vol. 19, No. 9, Apr. 25, 2011, pp. 8830-8838.
Yang et al., "Tunable Terahertz Wave Generation Through a Bimodal Laser Diode and Plasmonic Photomixer", Optics Express, vol. 23, No. 24, Nov. 30, 2015, pp. 31206-31215, doi: 10.1364/OE.23.031206.
Yardimci et al., "A High-Power Broadband Terahertz Source Enabled by Three-Dimensional Light Confinement in a Plasomic Nanocavity", Scientific Reports, vol. 7, No. 4166, Jun. 23, 2017, pp. 1-8, doi: 10.1038/s41598-017-04553-4.
Yardimci et al., "A High-Responsivity and Broadband Photoconductive Terahertz Detector Based on a Plasmonic Nanocavity", Applied Physics Letters, vol. 113, Dec. 18, 2018, 251102-1-251102-4, doi: https://doi.org/10.1063/1.5066243.
Yardimci et al., "High Sensitivity Terahertz Detection through Large-Area Plasmonic NanoAntenna Arrays", Scientific Reports, Feb. 16, 2017, vol. 7, Article 42667, pp. 1-8, doi: 10.1038/srep42667.
Yardimci et al., "High-Power Terahertz Generation Using Large-Area Plasmonic Photoconductive Emitters", IEEE Transactions on Terahertz Science and Technology, Mar. 2015, vol. 5, Issue 2, pp. 223-229, DOI: 10.1109/TTHZ.2015.2395417.
Yardimci et al., "Large Area Plasmonic Photoconductive Emitters for Generating High Power Broadband Terahertz Radiation", Frontiers in Optics, Tucson, Arizona United States, Oct. 19-23, 2014, https://doi.org/10.1364/FIO.2014.FTh3E.5.
Yardimci et al., "Nanostructure-Enhanced Photoconductive Terahertz Emission and Detection", Small, vol. 14, Issue 44, Nov. 2, 2018, first published Aug. 28, 2018, 14 pgs., doi.org/10.1002/smll.201802437l.
Yardimci et al., "Plasmonics Enhanced Terahertz Radiation from Large Area Photoconductive Emitters", IEEE, 2014, pp. 326-327, doi: 10.1109/IPCon.2014.6995376.
Yu et al., "The potential of terahertz imaging for cancer diagnosis: A review of investigations to date", Quantitative Imaging in Medicine and Surgery, Mar. 2012, vol. 2, No. 1, pp. 33-45, doi: 10.3978/j.issn.2223-4292.2012.01.04.
Zhang et al., "Simultaneous determination of amino acid mixtures in cereal by using terahertz time domain spectroscopy and chemometrics", Chemometrics and Intelligent Laboratory Systems, May 15, 2017, vol. 164, No. 15, pp. 8-15, DOI: 10.1016/j.chemolab.2017.03.001.
Zhong-Yuan et al., "Aflatoxin B1 detected by Terahertz time-domain spectroscopy", 8th International Congress on Image 7,8 and Signal Processing (LISP), IEEE, Oct. 14, 2015 (Oct. 14, 2015) pp. 1225-1230, XP032867276, DOI: 10.1109/CISP.2015.7408068.

* cited by examiner

METHODS AND SYSTEMS FOR DETECTING WATER STATUS IN PLANTS USING TERAHERTZ RADIATION

CROSS REFERENCE TO RELATED APPLICATIONS

This application is a national stage of PCT Patent Application No. PCT/US2020/058549, entitled "Methods and Systems for Detecting Water Status in Plants Using Terahertz Radiation" to Jarrahi et al., filed Nov. 2, 2020, which claims priority to U.S. Provisional Application Ser. No. 62/928,900, entitled "Methods and Systems for Detecting Water Status in Plants Using Terahertz Radiation" to Jarrahi et al., filed Oct. 31, 2019; the disclosure of which is herein incorporated by reference in its entirety.

FIELD OF THE INVENTION

The present invention is directed to systems and methods to detect water status in plants. In particular, systems and methods disclosed herein are directed to using terahertz imaging to determine water mass per leaf area, relative water content, and leaf water potential in plant tissue.

BACKGROUND OF THE INVENTION

Increases in the frequency and severity of droughts across many regions worldwide necessitates an improved capacity to determine the water status of plants at organ, whole plant, canopy and regional scales. Non-invasive methods have most potential for simultaneously improving basic water relations research and ground-, flight- and space-based sensing of water status, with applications in sustainability, food security and conservation. The most frequently used methods to measure the most salient proxies of plant water status, i.e., water mass per leaf area (WMA), relative water content (RWC), and leaf water potential (LP require the excision of tissues and lab analysis, and have thus been limited to relatively low throughput and small study scales.

Water within a plant absorbs electromagnetic radiation across the visible, infrared, and terahertz wavelengths distinctly from other structural plant components. (See e.g., Jones (2014) (cited above); and Knipling, (1970) Physical and physiological basis for the reflectance of visible and near-infrared radiation from vegetation. Remote Sensing of Environment 1: 155-159; the disclosure of which is herein incorporated by reference in its entirety.) Accordingly, many studies have shown correlations of radiation variables with leaf water status variables at the scale of individual leaves, whole plants and forest stands. (See e.g., Rapaport et al., (2017) The potential of the spectral 'water balance index' (WABI) for crop irrigation scheduling. New Phytologist 216: 741-757; Cotrozzi et al., (2017) Using foliar spectral properties to assess the effects of drought on plant water potential. Tree Physiology 37: 1582-1591; Rapaport et al., (2015) Combining leaf physiology, hyperspectral imaging and partial least squares-regression (PLS-R) for grapevine water status assessment. ISPRS Journal of Photogrammetry and Remote Sensing 109: 88-97; Sancho-Knapik et al., (2011) Microwave I-band (1730 MHz) accurately estimates the relative water content in poplar leaves. A comparison with a near infrared water index (R1300/R1450). Agricultural and Forest Meteorology 151: 827-832; Claudio et al., (2006) Monitoring drought effects on vegetation water content and fluxes in chaparral with the 970 nm water band index. Remote Sensing of Environment 103: 304-311; Penuelas and Inoue, (1999) Reflectance indices indicative of changes in water and pigment contents of peanut and wheat leaves. Photosynthetica 36: 355-360; Penuelas et al., (1993) The reflectance at the 950-970 nm region as an indicator of plant water status. International Journal of Remote Sensing 14: 1887-1905; Danson et al., (1992) High-spectral resolution data for determining leaf water content. International Journal of Remote Sensing 13: 461-470; Hunt and Rock, (1989) Detection of changes in leaf water content using near-and middle-Infrared reflectances. Remote Sensing of Environment 30: 43-54; and Hunt et al., (1987) Measurement of leaf relative water content by infrared reflectance. Remote sensing of environment 22: 429-435; the disclosures of which are herein incorporated by reference in their entireties.) The power of these approaches at large scales is shown by the use of airborne hyperspectral or microwave data to detect canopy water content across large forest ranges. (See e.g., Rao et al., (2019) Satellite-based vegetation optical depth as an indicator of drought-driven tree mortality. Remote Sensing of Environment 227: 125-136; and Asner et al., (2016) Progressive forest canopy water loss during the 2012-2015 California drought. Proceedings of the National Academy of Sciences 113: E249-E255; the disclosures of which are herein incorporated by reference in their entireties.) Yet, heretofore, the bulk of studies have focused on statistical correlations of water status variables across well hydrated and strongly dehydrated leaves, without clear resolution considering for mildly to moderately dehydrated leaves. Thus, further development is needed to sense WMA, RWC and $\Psi_{leaf}$ in mild and moderately dehydrated leaves, i.e., in the important range of leaf dehydration for the control of gas exchange, between full turgor and turgor loss point as well as at stronger levels of dehydration below turgor loss point. (See e.g., Trueba et al., (2019) Thresholds for leaf damage due to dehydration: declines of hydraulic function, stomatal conductance and cellular integrity precede those for photochemistry. New Phytologist 223: 134-49; and Bartlett et al., (2016) The correlations and sequence of plant stomatal, hydraulic, and wilting responses to drought. Proceedings of the National Academy of Sciences 113: 13098-13103; the disclosures of which are herein incorporated by reference in their entireties.)

SUMMARY OF THE INVENTION

Methods and systems for detecting water status in plants using terahertz imaging are disclosed.

In one embodiment, terahertz plant tissue sensing system includes a terahertz source configured to generate a terahertz beam having a frequency of approximately 100 GHz to approximately 10 THz, a terahertz detector configured to receive and record a terahertz signal, at least one optical element to guide the terahertz beam along an optical path from the terahertz source to the terahertz detector, where the optical path impinges on a target plant tissue to generate a signal from the target plant tissue, and an analyzer to determine at least one water status variable of the target plant tissue from the signal from the target plant tissue.

In a further embodiment, the system further includes a light source configured to generate an optical pulse focused to impinge the terahertz source, and where the terahertz beam is a terahertz pulse.

In another embodiment, the light source is a femtosecond laser.

In a still further embodiment, the light source is a Ti:Sapphire laser.

In still another embodiment, the system further includes a splitter and a delay stage, where the optical pulse passes through the splitter allowing a first beam to impinge the terahertz source and allowing a second beam passes through the delay stage en route to the terahertz detector.

In a yet further embodiment, the terahertz source is a plasmonic photoconductive nano-antenna array.

In yet another embodiment, the terahertz detector is a plasmonic photoconductive nano-antenna array.

In a further embodiment again, the system further includes a two-dimensional stage, where the target plant tissue is moved in two dimensions, where the terahertz source generates a plurality of terahertz beams, such that each beam in the plurality of terahertz beams impinges on a different location on the target plant tissue.

In another embodiment again, the analyzer determines the at least one water status variable by calculating a peak field ratio between a detected signal and a reference signal.

In a further additional embodiment, the at least one water status variable selected from the group consisting of water mass per area, relative water content, and water potential, the water mass per area is determined as a function of the peak field ratio, the relative water content is determined as the ratio between water mass per area and a saturated water mass per area, and the water potential ($\Psi_{leaf}$) is determined according to a pre-defined calibration curve or the formula: $\Psi_{leaf}=\Psi_S+\Psi_P$, where Ys is solute potential and $\Psi_P$ is pressure potential.

In another additional embodiment, the function of the peak field ratio is determined by obtaining a plurality of terahertz measurements from a plurality of leaves.

In a still yet further embodiment, the plurality of leaves possess include leaves having varying sizes, thicknesses, or stages of hydration.

In still yet another embodiment, the function of the peak field ratio is statistically modeled to resolve the water mass per area.

In a still further embodiment again, the statistically modeling is performed using an ordinary least squares regression.

In still another embodiment again, the plurality of leaves are from a single species.

In a still further additional embodiment, the plurality of leaves are from multiple species.

In still another additional embodiment, solute potential ($\Psi$s) and pressure potential ($\Psi_P$) are calculated as:

$$\Psi_S = \frac{\pi_o \cdot \Psi_{tlp}(1-RWC_{tlp})}{\pi_o(1-RWC)+\Psi_{tlp}(RWC-RWC_{tlp})}$$

and:

$$\Psi_P = \begin{cases} \pi_o \cdot \left(\frac{RWC-RWC_{tlp}}{1-RWC_{tlp}}\right), & \text{if } RWC > RWC_{tlp} \\ 0, & \text{if } RWC < RWC_{tlp} \end{cases}$$

where $\pi_o$ is the osmotic potential at full turgor, RWC is the determined relative water content, $\Psi_{tlP}$ is water potential at turgor los point, and $RWC_{tlp}$ is the relative water content at turgor loss point.

In a yet further embodiment again, the signal from the target plant tissue is a reflected signal.

In yet another embodiment again, a method for the terahertz imaging of plant tissue includes illuminating a target plant tissue with a terahertz pulse to produce a signal therefrom, where the terahertz pulse has a frequency of approximately 100 GHz to approximately 10 THz, detecting the signal using a terahertz detector, and determining at least one water status variable by calculating a peak field ratio between the detected signal and a reference signal.

In a yet further additional embodiment, the method further includes generating the terahertz pulse by illuminating a terahertz source with a light source.

In yet another additional embodiment, the light source is a femtosecond laser.

In a further additional embodiment again, the light source is a Ti:Sapphire laser.

In another additional embodiment again, the illuminating step comprises illuminating the target plant tissue with a plurality of terahertz pulses, where each pulse in the plurality of terahertz pulses impinges on a different location on the target plant tissue.

In a still yet further embodiment again, the at least one water status variable selected from the group consisting of water mass per area, relative water content, and water potential, the water mass per area is determined as a function of the peak field ratio, the relative water content is determined as the ratio between water mass per area and a saturated water mass per area, and the water potential ($\Psi$leaf) is determined according to a pre-defined calibration curve or the formula: $\Psi_{leaf}=\Psi_S+\Psi_P$, where $\Psi_S$ is solute potential and $\Psi_P$ is pressure potential.

In still yet another embodiment again, the function of the peak field ratio is determined by obtaining a plurality of terahertz measurements from a plurality of leaves.

In a still yet further additional embodiment, the plurality of leaves possess include leaves having varying sizes, thicknesses, or stages of hydration.

In still yet another additional embodiment, the function of the peak field ratio is statistically modeled to resolve the water mass per area.

In a yet further additional embodiment, the statistically modeling is performed using an ordinary least squares regression.

In yet another additional embodiment again, the plurality of leaves are from a single species.

In a still yet further additional embodiment again, the plurality of leaves are from multiple species.

In still yet another additional embodiment again, solute potential (LPs) and pressure potential ($\Psi_P$) are calculated as:

$$\Psi_S = \frac{\pi_o \cdot \Psi_{tlp}(1-RWC_{tlp})}{\pi_o(1-RWC)+\Psi_{tlp}(RWC-RWC_{tlp})}$$

and:

$$\Psi_P = \begin{cases} \pi_o \cdot \left(\frac{RWC-RWC_{tlp}}{1-RWC_{tlp}}\right), & \text{if } RWC > RWC_{tlp} \\ 0, & \text{if } RWC < RWC_{tlp} \end{cases}$$

where $\pi_o$ is the osmotic potential at full turgor, RWC is the determined relative water content, $\Psi_{tlp}$ is water potential at turgor los point, and $RWC_{tlp}$ is the relative water content at turgor loss point.

In another further embodiment, an irrigation system includes a terahertz plant tissue sensing system to determine water status of a target plant, a water distribution system, and a controller for controlling the water distribution system based on the water status determined by the terahertz plant tissue sensing system.

In still another further embodiment, the water distribution system is selected from the group consisting of: a sprinkler, a sprayer, and a linear irrigation system.

In yet another further embodiment, the controller is managed by a machine learning algorithm to automatically control the water distribution system.

In another further embodiment again, a method of calibrating a terahertz system for measuring water status of plant tissue includes obtaining a plurality of leaves from a plant, where each leaf in the plurality of leaves are obtained at various stages of dehydration, determining a relative water content for the plurality of leaves, and constructing a species-specific pressure-volume curve for the plant, where the species-specific pressure-volume curve can be used to extract a plurality of parameters, including turgor loss point, osmotic potential at full turgor, and relative water content values at turgor loss point.

Another further additional embodiment, the relative water content is determined by:

$$RWC = \frac{FM - DM}{SM - DM}$$

where FM is the mass of a particular leaf as harvested at a particular stage of dehydration and SM is the intercept of standard major axis regression lines fitted for the relationship between the leaf water mass and deaf.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and other features and advantages of the present invention will be better understood by reference to the following detailed description when considered in conjunction with the accompanying drawings where.

DETAILED DISCLOSURE OF THE INVENTION

Figure 1:
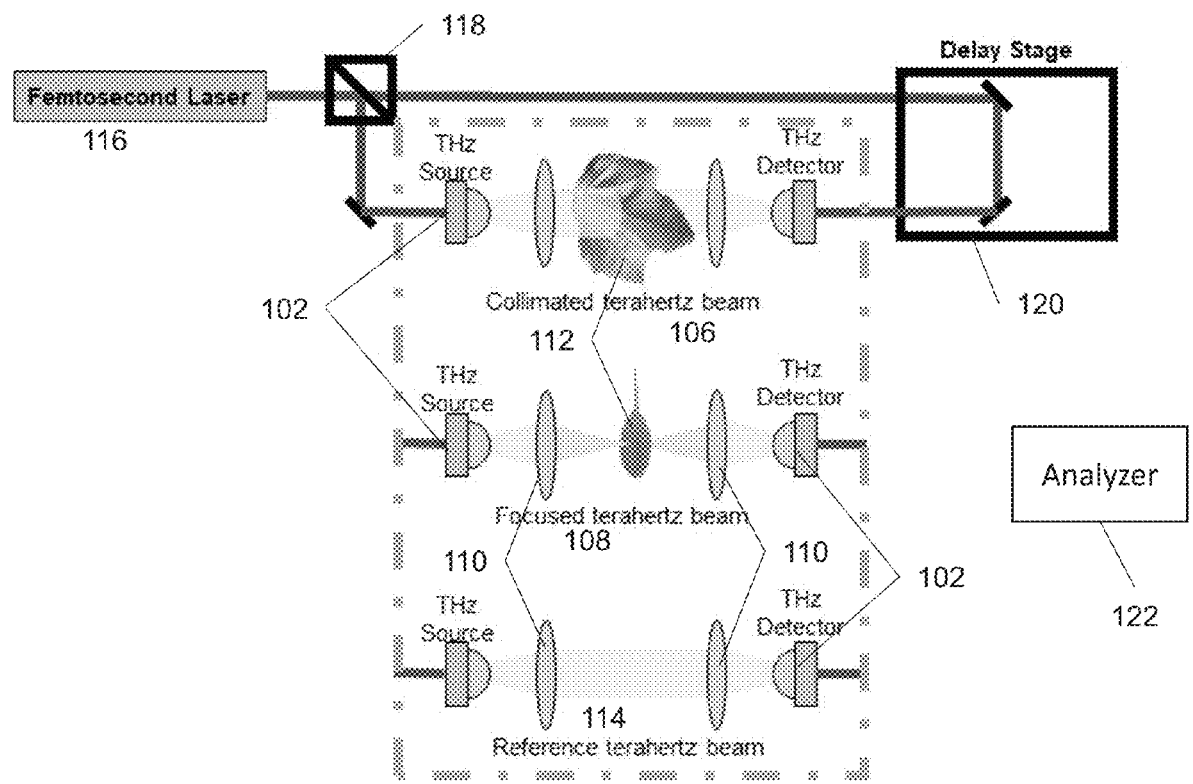
FIG. 1 illustrates a schematic of the terahertz time-domain spectroscopy and its output in accordance with various embodiments of the invention.

The embodiments of the invention described herein are not intended to be exhaustive or to limit the invention to precise forms disclosed. Rather, the embodiments selected for description have been chosen to enable one skilled in the art to practice the invention.

Turning to the data and drawings, systems and methods are provided which utilize THz illumination to detect water status in plants. In many embodiments, assessment of multiple measurements at terahertz frequencies is used to provide a determination of water status variables, including water mass per leaf area (WMA), relative water content (RWC), and leaf water potential ($\Psi_{leaf}$). Many embodiments described herein use a THz-TDS system to characterize the terahertz transmission peak field ratio (PFR) for leaves at various hydration states (e.g., various levels of dehydration), thus determining key water status variables (e.g., WMA, RWC, and $\Psi_{leaf}$). In particular, many embodiments use terahertz radiation for the determination of WMA, RWC and $\Psi_{leaf}$ during mild, moderate and severe leaf dehydration. Numerous embodiments allow for the determination of water status for leaves of a single species and/or across multiple species using physical relationships.

Understanding plant responses to water is increasingly urgent given drought-induced losses in crop productivity and tree mortality in many ecosystems worldwide. (See e.g., Allen et al., (2010) A global overview of drought and heat-induced tree mortality reveals emerging climate change risks for forests. Forest Ecology and Management 259: 660-684; and IPCC, (2014) Climate change 2014: synthesis report. Contribution of working groups I, II and III to the fifth assessment report of the intergovernmental panel on climate change, Ed 5. IPCC, Geneva, Switzerland; the disclosures of which are herein incorporated by reference in their entireties.) Improving the capacity to determine tissue water status at organ, whole plant, canopy and regional scales is necessary to resolve the drought responses and water requirements of crop and wild species, for food security and agricultural and urban sustainability of water use.

The most salient metrics of leaf water status at leaf scale are water mass per leaf area (WMA; numerically equal to the "leaf equivalent water thickness"), relative water content (RWC) and leaf water potential ($\Psi_{leaf}$). (See e.g., Tucker (1980) Remote sensing of leaf water content in the near infrared. Remote sensing of Environment 10: 23-32; Hunt and Rock (1989) Detection of changes in leaf water content using near-and middle-Infrared reflectances. Remote Sensing of Environment 30: 43-54; and Jones (2014) Plants and Microclimate, 3rd ed. Cambridge University Press, Cambridge, United Kingdom; the disclosures of which are herein incorporated by reference in their entireties.) These indices are correlated for a given dehydrating leaf, and provide different information. Whereas WMA represents the absolute tissue water content normalized by leaf area, RWC, normalized by the saturated water content, also provides information of cell volume shrinkage and thereby captures more specifically the plant-experienced water stress. (See e.g., Sack et al., (2018) ABA accumulation in dehydrating leaves is associated with decline in cell volume, not turgor pressure. Plant Physiology 176: 489-495; the disclosure of which is herein incorporated by reference in its entirety.) Even more mechanistic insight is provided by $\Psi_{leaf}$, which enables quantification of the balance of osmotic and turgor pressures, and represents the driving force for water movement, enabling estimation of hydraulic conductances. (See e.g., Scoffoni et al., (2018) The causes of leaf hydraulic vulnerability and its influence on gas exchange in *Arabidopsis thaliana*. Plant Physiology: pp. 00743.02018; Bartlett et al., (2012) The determinants of leaf turgor loss point and prediction of drought tolerance of species and biomes: a global meta-analysis: Drivers of plant drought tolerance. Ecology Letters 15: 393-405; and Scoffoni et al., (2012) Dynamics of leaf hydraulic conductance with water status: quantification and analysis of species differences under steady state. Journal of Experimental Botany 63: 643-658; the disclosures of which are herein incorporated by reference in their entireties.) However, typical methods for measuring these variables require the excision of tissues and lab analysis, either gravimetric in the case of WMA and RWC, or using the Scholander pressure chamber or psychrometry for $\Psi_{leaf}$, and thus measurement of plant water status has often been limited to relatively low throughput and small study scales. (Jones (2014); cited above.) By contrast, non-invasive methods have great potential for improving ground-based and remote sensing in water relations research and their applications in agriculture and conservation, especially as WMA, RWC and $\Psi_{leaf}$ can in principle be estimated not only for leaves, but also at coarser scales, for whole canopies. Embodiments described herein provide methods and systems to estimate WMA, RWC, and deaf from terahertz radiation. Many embodiments are able to provide these measures during mild, moderate and severe leaf dehydration, for given leaves, across leaves of a given species, or across multiple species.

Electromagnetic radiation in the terahertz regime (approximately 100 GHz (e.g., ±25 GHz) to approximately 10 THz (e.g., ±1 THz) frequency range or approximately 10 µm (e.g., ±2.5 µm) to approximately 1,000 µm (e.g., ±100 µm) wavelength range). Transitions between vibrational and rotational states of many polar molecules, such as water, fall in the terahertz region of the electromagnetic, and thus, terahertz wave propagation is very sensitive to the sample water content. (See e.g., Hecht, (2002) Optics. Addison-Wesley, Reading, Massachusetts; Ronne et al., (1999) THz spectroscopy of liquid H2O and D20. Physical Review Letters 82: 2888-2891; Mittleman et al., MC (1998) Gas sensing using terahertz time-domain spectroscopy. Applied Physics B 67: 379-390; Mittleman et al., (1996) T-ray imaging. IEEE Journal of selected topics in quantum electronics 2: 679-692; and Thrane et al., (1995) THz reflection spectroscopy of liquid water. Chemical Physics Letters 240: 330-333; the disclosures of which are herein incorporated by reference in their entireties.) In addition, terahertz radiation can offer higher resolution imaging compared to microwave frequencies. Imaging and spectroscopy at terahertz frequencies are harmless since the energy of the photon is very small, compared to lower-wavelength radiation such as ultraviolet and X-rays. (See e.g., Sun et al., (2011) A promising diagnostic method: Terahertz pulsed imaging and spectroscopy. World journal of radiology 3: 55-65; the disclosure of which is herein incorporated by reference in its entirety.) Terahertz time domain spectroscopy (THz-TDS) employs short pulses of electromagnetic radiation, which have a broad terahertz frequency range. (See e.g., Skoog et al., (2017) Principles of instrumental analysis. Cengage learning; the disclosure of which is herein incorporated by reference in its entirety.) The transmitted and reflected pulses through and from the sample are detected to extract the time- and frequency-domain responses. (See e.g., Yardimci et al., (2017) A high-power broadband terahertz source enabled by three-dimensional light confinement in a plasmonic nanocavity. Scientific Reports 7: 4166; and Yardimci and Jarrahi, (2017) High sensitivity terahertz detection through large-area plasmonic nano-antenna arrays. Scientific Reports 7: 42667; the disclosures of which are herein incorporated by reference in their entireties.) Because of these specifications, there has been great interest in predicting plant water status using THz-TDS systems. (See e.g., Gente et al., (2018) Outdoor measurements of leaf water content using THz quasi time-domain spectroscopy. Journal of Infrared, Millimeter, and Terahertz Waves 39: 943-948; Baldacci et al., (2017) Non-invasive absolute measurement of leaf water content using terahertz quantum cascade lasers. Plant Methods 13; Santesteban et al., (2015) Terahertz time domain spectroscopy allows contactless monitoring of grapevine water status. Frontiers in Plant Science 6; Gente et al., (2015) Contactless water measurements on plants at 35 GHz. Journal of Infrared, Millimeter, and Terahertz Waves 36: 312-317; Born et al., (2014) Monitoring plant drought stress response using terahertz time-domain spectroscopy. Plant Physiology 164: 1571-1577; Gente et al., (2013) Determination of leaf water content from terahertz time-domain spectroscopic data. Journal of infrared, millimeter, and terahertz waves 34: 316-323; Castro-Camus et al., (2013) Leaf water dynamics of *Arabidopsis thaliana* monitored in-vivo using terahertz time-domain spectroscopy. Scientific Reports 3; Jördens et al., (2009) Evaluation of leaf water status by means of permittivity at terahertz frequencies. Journal of Biological Physics 35: 255-264; Hadjiloucas et al., (1999) Measurements of leaf water content using terahertz radiation. IEEE Transactions on Microwave Theory and Techniques 47: 142-149; and Hu and Nuss, (1995) Imaging with terahertz waves. Optics letters 20: 1716-1718; the disclosures of which are herein incorporated by reference in their entireties.) However, as for other wavelengths, previous terahertz studies have generally compared only well hydrated versus strongly dehydrated leaves in absolute water content, WMA, or deaf with limited resolution for moderately dehydrated leaves. (See e.g., Gente et al., (2018, cited above); Li et al., (2018) Measurements and analysis of water content in winter wheat leaf based on terahertz spectroscopy. International Journal of Agricultural and Biological Engineering 11: 178-182; Baldacci et al., (2017, cited above); Born et al., (2014, cited above); Gente et al., (2013, cited above); Castro-Camus et al., (2013, cited above); Jördens et al., (2009, cited above); and Hadjiloucas et al., (1999, cited above); the disclosures of which are herein incorporated by reference in their entireties.) While physical models have been proposed to relate absolute water content or WMA to terahertz absorption, these models have not yet extended to enable scaling to RWC and $\Psi_{leaf}$. (See e.g., Baldacci et al., (2017, cited above); Gente et al., (2013, cited above); and Jördens et al., (2009, cited above).)

Turning to FIG. 1, a schematic of systems in accordance with some embodiments is illustrated. In some embodiments, a terahertz source 102 is configured to generate a terahertz beam which are guided along an optical path to a terahertz detector 104. In some embodiments, the terahertz beam is a pulse, such that the illumination beam is transmitted for a limited time suitable for time domain spectroscopy. In many embodiments, the terahertz detector 104 is configured to receive and record a terahertz signal. In various embodiments, the terahertz detector 104 is configured to receive s spectrum of frequencies. In certain embodiments, the terahertz illumination beam is guided and focused on the terahertz detector 104. In some embodiments, the guiding and focusing uses at least one optical element 110 aligned in an optical path between the terahertz source 102 and the terahertz detector 104. In certain embodiments, an optical element is configured to create collimated 106 or focused 108 optical path prior to guiding and focusing a terahertz illumination beam onto a terahertz detector 104. In certain embodiments, the collimated 106 or focused 108 optical path impinges on a target plant tissue 112, such as a leaf, stem, flower, peduncle, sepal, or other plant anatomy. In some embodiments, the terahertz detector 104 detects terahertz transmission, reflectance, and/or emission from the target plant tissue 112.

Additional embodiments include a reference beam 114 that possesses an optical path (either collimated or focused) that does not pass through plant tissue. Some embodiments do not include a separate reference beam 114, but instead generate reference data by detecting a terahertz beam without any sample placed in the optical path of the terahertz beam.

In a number of embodiments, the terahertz beam is generated by generating an optical pulse from a light source 116, such as a femtosecond laser, where the optical pulse is focused to impinge the terahertz source 102 to allow the terahertz source 102 to generate a terahertz pulse. In certain embodiments, the light source 116 is a Ti:Sapphire laser (e.g., Coherent MIRA0HP, Coherent Inc., Santa Clara, USA). In some embodiments, the optical pulses are generated as femtosecond pulses at a 780 nm wavelength. In many embodiments, the optical pulse generated by light source 116 pumps the terahertz source 102 to generate the terahertz pulses. In many embodiments, the terahertz source 102 is a plasmonic photoconductive nano-antenna array to provide high power terahertz radiation sensitivity over a broad terahertz frequency range. Similarly, the terahertz detector 104 can also be a plasmonic photoconductive nano-antenna array to provide high terahertz detection sensitivity over a broad terahertz frequency range. (See Yardimci and Jarrahi, (2017, cited above); and Yardimci (2015, cited above).) In a number of embodiments using a light source, the resultant beam is split using a splitter 118, which allows a first beam to impinge on and/or pump a terahertz source 102, while a second beam passes through a linear delay stage 120 en route to the terahertz detector 104. In a number of embodiments, by moving the linear delay stage 120 and changing the time delay between the optical pump and probe pulses incident on the terahertz source 102 and terahertz detector 104, respectively, the time-domain electric field profile of the terahertz pulses incident on the terahertz detector 104 can be resolved with a sub-picosecond resolution over a 400 ps time-window. While the above portions describe terahertz pulse detection from transmission of a signal through a sample, a number of embodiments detect terahertz pulses as reflectance from plant tissue.

To further increase the signal-to-noise-ratio of the resolved signal in many embodiments, multiple time-domain traces (e.g., approximately 10 traces) can be captured and averaged. By taking the Fourier transform of the averaged time-domain signal, the frequency-domain data can be obtained with a 2.5 GHz frequency resolution. In various embodiments, the THz-TDS system used for measurements offers a 100-dB dynamic range and a frequency range of approximately 0.1 THz (e.g., ±10%) to approximately 5.5 THz (e.g., ±10%).

Further embodiments include an analyzer 122 to determine at least one water status variable, such as water mass per area (WMA), relative water content (RWC), and water potential (Y) of the target plant tissue. Determining at least one water status variable in accordance with many embodiments is further discussed below. In various embodiments, the analyzer is any suitable dedicated or software-based device capable of determining a water status variable from a terahertz signal. In various embodiments, an analyzer 122 is in communication (e.g., wired or wireless) with a terahertz detector 104, such that detected signals are transmitted directly to the analyzer 122, while in some embodiments, an analyzer 122 is provided recorded signals from a terahertz detector 104.

While many plant tissues (e.g., leaves) can vary greatly in size between species, the optical path of a terahertz pulse can be collimated or focused (e.g., a collimated path may work better for species with large leaves, while a focused path may work better for species with smaller leaves). Additionally, many embodiments use a two-dimensional stage (e.g., XY translation stage) to allow multiple measurements over an area. In such embodiments, a two-dimensional stage moves the target plant tissue in two dimensions (e.g., X- and Y-axes) to allow an individual beams or pulses to impinge the tissue at different positions, thus creating a plurality of signals from the target plant tissue. For example, a plurality of terahertz pulses can be illuminated over a grid pattern, such as a 5 mm×5 mm grid with measurements taken at 1 mm steps to be able to measure a terahertz signal at multiple points. Additionally, in focused paths, the beam spot can have a smaller diameter (e.g., ~3 mm diameter), which can allow for smaller grids and steps, (e.g., 6 mm×6 mm with 0.5 mm steps). The smaller diameter of a focused beam, can allow for a higher resolution imaging, but this advantage would come with increased measurement times. In additional embodiments, a collimated path, which generally have a wider beam (e.g., ~1.5 cm diameter), can be used to collect a plurality signals from the target plant tissue across a larger area simultaneously. Additional embodiments utilize multi-pixel scanners to acquire measurements over a grid pattern. In multi-pixel embodiments, the plurality of signals arising from the plant tissue can then be averaged.

Determining Water Status with Terahertz Signals

Figure 2:
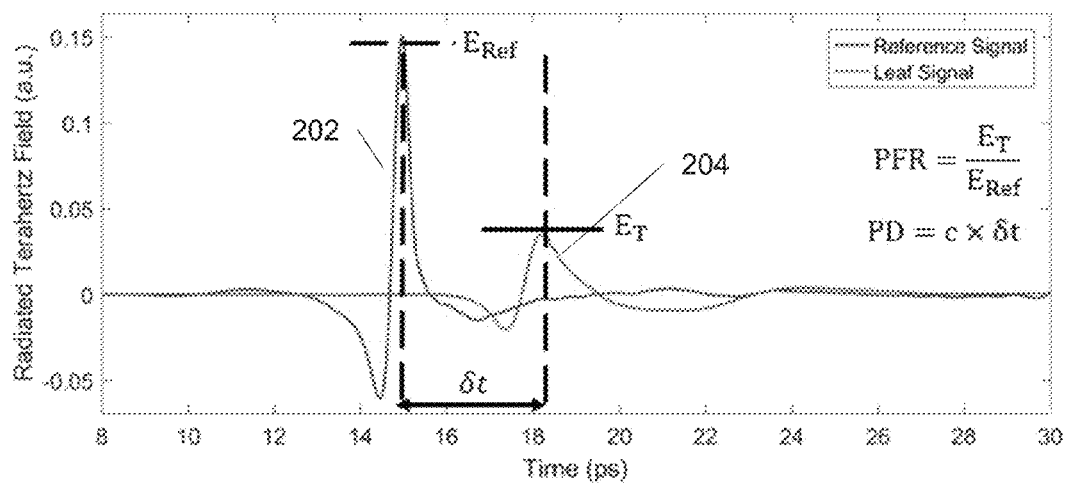
FIG. 2 illustrates a time-domain reference signal along with a signal transmitted through a sample in accordance with embodiments of the invention.

Turning to FIG. 2, an exemplary terahertz signal in accordance with some embodiments is illustrated. In FIG. 2, a reference pulse produces a reference signal peak 202 in the output of a terahertz detector, while a terahertz pulse passing through a sample produce a sample signal peak 204 in the output of a terahertz detector in a variety of embodiments. As noted herein, many embodiments are directed to systems and methods that use the scanning method in combination with terahertz imaging to sense and map hydration in plant tissue, providing a solution to identifying plant conditions in drought and/or other water-stressed conditions.

During measurement, the reference terahertz signal of many embodiments has a peak electric field amplitude of $E_{Ref}$, while the sample produces a peak electric field amplitude of $E_T$. (See e.g., Hecht (2002, cited above).) Additionally, a time delay between the reference 202 and sample 204 signals is represented as $\delta_t$, as annotated in FIG. 2. Additionally, the electromagnetic radiation is partially reflected from the leaf surface and partially absorbed within the leaf. The absorbed terahertz radiation can be estimated by comparing the time-domain reference signal with that obtained after transmission through the leaf. In many embodiments, the peak field ratio (PFR) used to estimate leaf water status (FIG. 2) is calculated as:

$$PFR = \frac{\max(E_T)}{\max(E_{Ref})} \quad (1)$$

The amplitude of the transmitted terahertz field has a strong dependence on the total absorbed power within the leaf over a broad terahertz frequency range. In a number of embodiments, the relationship between the peak amplitudes of the reference and transmitted terahertz fields is estimated as:

$$|E_T|=|E_{Ref}| \cdot |1-R| \cdot e^{-\alpha d} \quad (2)$$

where R and a are respectively assumed to be the reflectivity and the absorption coefficient effective across the measured terahertz frequency band, and d to be the leaf thickness. (See e.g., Hecht (2002, cited above).) The absorption coefficient, $\alpha$, has a strong dependence on the thickness of water within the leaf, as determined by:

$$\alpha = \frac{WT \cdot \alpha_W + VT \cdot \alpha_V + ST \cdot \alpha_S}{WT + VT + ST} \quad (3)$$

where WT is the thickness of water in the leaf, VT is the thickness of the vapor-saturated leaf airspaces, ST is the thickness of other non-air leaf materials; $\alpha w$, $\alpha v$, and $\alpha s$ are the absorption coefficients of liquid water, vapor and other non-water (solid or dissolved) leaf materials. In a variety of embodiments, the absorption coefficients used in equations 1-3 are assumed to be an average value over terahertz frequency bandwidth of the THz-TDS system used for these measurements. Combining equations 2 and 3 with d=WT+VT+ST, reveals:

$$|E_T|=|E_{Ref}| \cdot |1-R| \cdot e^{-(WT \cdot \alpha_W + VT \cdot \alpha_V + ST \cdot \alpha_S)} \quad (4)$$

To relate the measured PFR values to measured leaf water status, both sides of equation 4 can be divided by $|E_{Ref}|$, PFR can be substituted for $$\frac{E_T}{E_{Ref}}$$

using equation 1, and ln-transformed, revealing:

$$\ln(PFR)=\ln(|1-R|)-WT \cdot \alpha_W-VT \cdot \alpha_V-ST \cdot \alpha_S \quad (5)$$

In many embodiments, it is assumed that WT and VT are similar magnitude, $\alpha v \ll \alpha w$, and VT av are negligible. (See e.g., Yang et al., (2011) Measurement of the transmission of the atmosphere from 0.2 to 2 THz. Optics express, 19: 8830-8838; Ronne et al., (1999, cited above); and Kindt and Schmuttenmaer, (1996). Far-infrared dielectric properties of polar liquids probed by femtosecond terahertz pulse spectroscopy. The Journal of Physical Chemistry 24: 10373-10379; the disclosures of which are herein incorporated by reference in their entireties.) Thus, in a variety of embodiments, solving for WT reveals:

$$WT = \frac{-\ln(PFR)}{\alpha_W} + \frac{\ln(|1-R|) - ST \cdot \alpha_S}{\alpha_W} \quad (6)$$

A number of embodiments assume that aw, av, as, ST, and as remain constant. Additionally, R can be assumed to remain constant. (See e.g., Sun et al. (2011, cited above).) Thus, a number of embodiments determine WT as a linear function of ln PFR as:

$$WT = \frac{-\ln(PFR)}{\alpha_W} + c \quad (7)$$

$$\text{where } c = \frac{\ln(|1-R|) - ST \cdot \alpha_S}{\alpha_W}$$

Notably, the density of water equals 1.0 g/cm³, and that water thickness (WT) is equivalent to water volume per unit leaf area, WT is numerically equivalent to the total leaf water mass per area (WMA). Thus, for a number of embodiments, each leaf of a particular species can be statistically modeled to resolve WMA as a function of PFR. In some embodiments, the WMA is fitted to lines as a linear function of ln PFR, e.g.:

$$WMA = \alpha \cdot \ln PFR + b \quad (8)$$

In further embodiments, the fitted lines are used, WMA values are determined from PFR, i.e., $\widehat{WMA}$. To determine relative water content $\widehat{RWC}$ in many embodiments, the determined WMA values are divided by the saturated water mass per area for each leaf (SWMA) as:

$$\widehat{RWC} = \frac{\widehat{WMA}}{SWMA} \quad (9)$$

Notably, SWMA=LMA·SWC, where SWC is the saturated water content, i.e., the water mass in saturated leaf divided by leaf dry mass, and LMA is the leaf mass per area of the leaf. Methods to determine LMA and SWC are further described below in reference to equations 13-15 and the surrounding text.

Additional embodiments determine $\Psi_{leaf}$ from $\widehat{RWC}$ using pressure volume curve parameters derived from curves fitted according to pressure volume theory. (See e.g., Sack et al., (2018, cited above).) $\Psi_{leaf}$ is the sum of the pressure potential ($\Psi_P$) and the solute potential ($\Psi$s):

$$\Psi_{leaf} = \Psi_S + \Psi_P \quad (10)$$

and:

$$\Psi_S = \frac{\pi_o \cdot \Psi_{tlp}(1-RWC_{tlp})}{\pi_o(1-RWC) + \Psi_{tlp}(RWC-RWC_{tlp})} \quad (11)$$

Where $\Pi_o$, $RWC_{tlp}$ and $\Psi_{tP}$ were determined from pressure volume curves as described herein, and:

$$\Psi_P = \begin{cases} \pi_o \cdot \left( \frac{RWC - RWC_{tlp}}{1 - RWC_{tlp}} \right), & \text{if } RWC > RWC_{tlp} \\ 0, & \text{if } RWC < RWC_{tlp} \end{cases} \quad (12)$$

Thus, using this physical model, a number of embodiments determine $\widehat{WMA}$, $\widehat{RWC}$, and $\widehat{\Psi_{leaf}}$ from terahertz measurements.

Measuring LMA, RWC, and SWC

In order to calibrate systems for measuring water status in plants, a number of embodiments calibrate the system based on determinations of LMA, RWC, and SWC for a given species. In these embodiments, plant tissue (e.g., a leaf) are obtained. In a number of embodiments, the plant tissue is obtained as the plant is being dehydrated, such that plant tissue is obtained at various stages of dehydration. In many embodiments, leaf mass per area is a determination of the ratio between leaf dry mass (DM) and leaf lamina area (LA), as represented by:

$$LMA = \frac{DM}{LA} \tag{13}$$

Dry mass for a particular leaf can be determined by drying or desiccating a leaf to extract all or virtually all water from a particular leaf. A number of embodiments utilize oven drying, while other embodiments utilize lyophilization. Oven drying can be accomplished by drying the leaf at 70° C. for 48 h. Leaf lamina area can be determined a number of ways, such as through the use of an imaging system (e.g., camera and/or flatbed scanner) followed by measuring the area, such as through the use of software, including Fiji, which are designed to make such calculations. (See e.g., Schindelin et al., (2012) Fiji: an open-source platform for biological-image analysis. Nature Methods 9: 676; the disclosure of which is herein incorporated by reference in its entirety.)

A number of embodiments determine relative water content (RWC) for various stages of dehydration according to:

$$RWC = \frac{FM - DM}{SM - DM} \tag{14}$$

Where FM is the fresh leaf mass and SM is the saturated mass of the particular leaf. Fresh leaf mass is the mass of the leaf as harvested at a particular stage of dehydration, while the saturated mass is determined in several embodiments as the intercept of standard major axis regression lines fitted for the relationship between the leaf water mass and $\Psi_{leaf}$. (See e.g., Sack and Pasquet-kok, (2011) Leaf pressure-volume curve parameters. In. PromethusWiki; the disclosure of which is herein incorporated by reference in its entirety.)

And, saturated water content (SWC) in a number of embodiments is determined as:

$$SWC = \frac{SM}{DM} \tag{15}$$

Further embodiments construct species-specific pressure-volume curves using RWC and $\Psi_{leaf}$ data for leaves having data points more negative than turgor loss point. (See e.g., Scoffoni et al., (2018, cited above).) From the pressure volume curves, additional embodiments extract parameters, including turgor loss point ($\Psi_{tlp}$), osmotic potential at full turgor ($\Pi_o$), and relative water content values at turgor loss point ($RWC_{tlp}$). (See e.g., Sack and Pasquet-kok, (2011, cited above).)

Methods to Determine Water Status

Figure 3A:
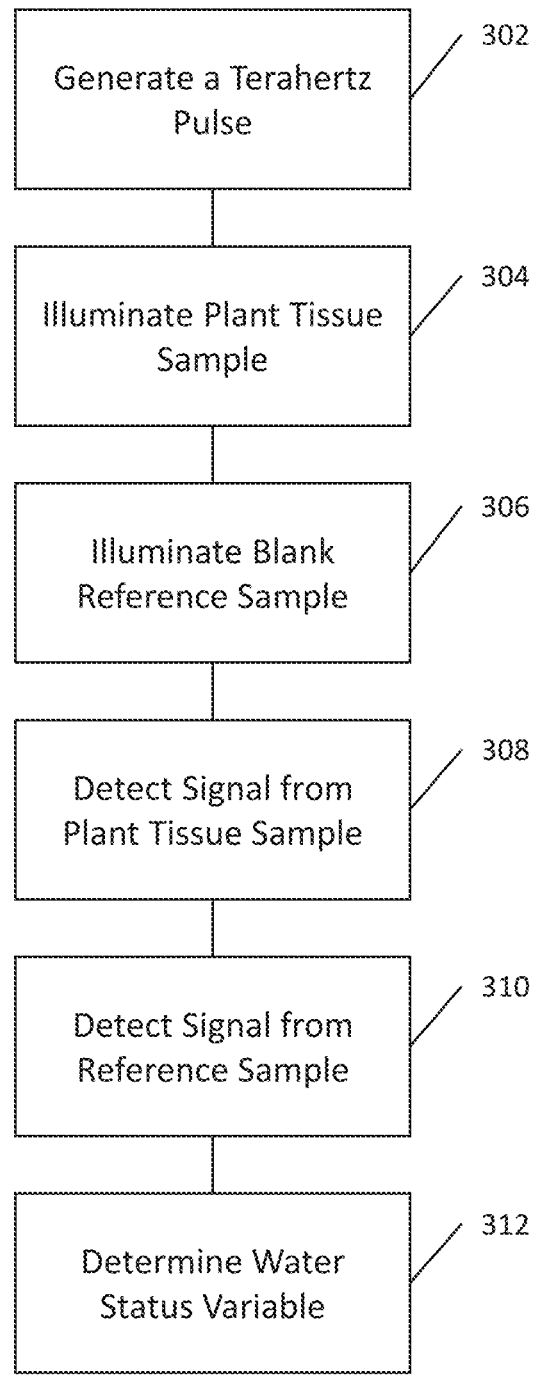
FIG. 3A illustrates a method to determine water content of plant tissue in accordance with various embodiments of the invention.

Turning to FIG. 3A, an exemplary method 300 to determine water status in a plant tissue is illustrated. At 302, certain embodiments generate at least one terahertz pulse using a terahertz source. As noted elsewhere herein, a terahertz pulse is a frequency from approximately 100 GHz to approximately 10 THz.

In some embodiments, plant tissue sample is illuminated by a terahertz pulse to produce a signal from the plant tissue sample 304. In various embodiments, the plant tissue sample is illuminated with a plurality of terahertz pulses, such as by illuminating a grid pattern. The signal from the plant tissue sample can be reflected light, transmitted light, and/or emitted light from the plant tissue sample. In various embodiments, the plant tissue sample is selected from leaf, flower, stem, peduncle, or other plant tissue. Additionally, some embodiments illuminate a blank sample pathway to obtain a reference signal at 306. As noted elsewhere herein, the reference signal can be via a separate pathway, while some embodiments obtain a blank reading from the sample pathway without a sample located within the pathway At 308, many embodiments detect the signal from the plant tissue sample using a terahertz detector, such as described elsewhere herein. In embodiments illuminating the plant tissue sample with a plurality of pulses, a plurality of signals are detected, and the plurality of received signals can be averaged. Additionally, at 310, certain embodiments detect a reference signal from a blank sample chamber or pathway.

Additionally, at 312 many embodiments determine at least one water status variable for the plant tissue. As noted elsewhere herein, water status variables include water mass per area, relative water content, and water potential. Determining a water status variable can be accomplished via the time domain spectroscopy (e.g., THz-TDS) as described elsewhere herein, including through the use of equations 1-12.

Methods to Calibrate a Terahertz System

Figure 3B:
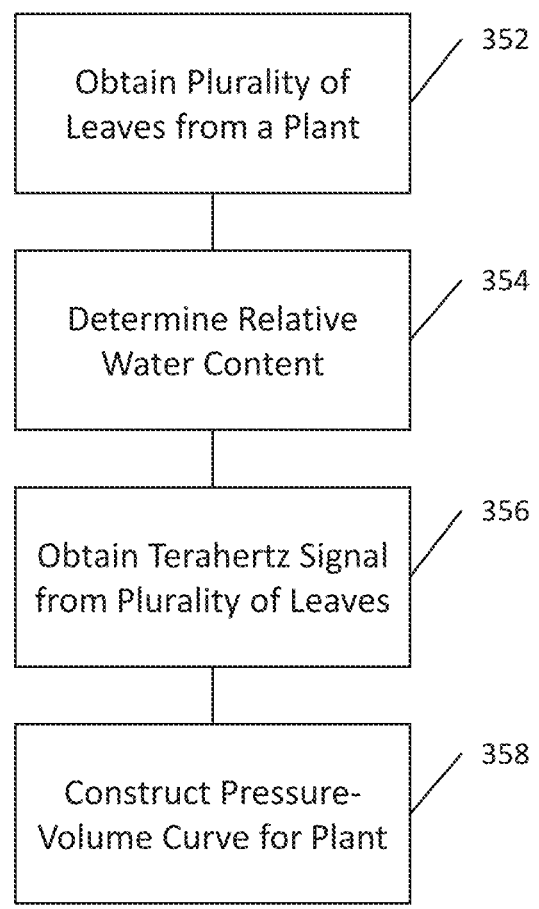
FIG. 3B illustrates a method to calibrate a terahertz system for measuring water status of plant tissue in accordance with various embodiments of the invention.

Turning to FIG. 3B, an exemplary method 350 to calibrate a terahertz system for determining water status is illustrated. In method 350, various embodiments obtain a plurality of leaves from a plant at 352. In some embodiments, the leaves possess varying stages of hydration or dehydration (e.g., 100% hydration is 0% dehydration, 50% hydration is 50% dehydration, and 0% hydration is 100% dehydration), size, and/or thickness. In certain embodiments the plurality of leaves are obtained from a single species, while other embodiments obtain the plurality of leaves from a plurality of species (either a plurality of leaves from each species in the plurality of species or a single leaf from each species in the plurality of species). In various embodiments, a relative water content is determined at 354. In many embodiments, determining relative water content is determined by methods such as those described herein. At 356, many embodiments obtain a plurality of terahertz measurements from the plurality of leaves, through such methods and systems describe elsewhere herein. Various embodiments obtain a plurality of measurements from a single leaf, while some embodiment obtain a single measurement from each of a plurality of leaves. Additional embodiments obtain a plurality of measurements from each leaf in a plurality of leaves. Finally, at 358, further embodiments construct a species-specific pressure-volume curve for the plant based on the relative water content for the particular terahertz system. In many embodiments, a species-specific pressure-volume curve can be used to extract a plurality of parameters, including turgor loss point, osmotic potential at full turgor, and relative water content values at turgor loss point.

Further Embodiments to Detect Water Status

Many embodiments describe non-invasive methods to determine water status in plants using terahertz radiation. While many of the embodiments discussed herein describe methods to measure water status using terahertz transmission through plant tissue, one of skill in the art would understand that these methods can be adjusted to determine water status through reflectance of a terahertz signal. As such, various embodiments incorporating these methods are able to determine water status through at least one of terahertz transmission and terahertz reflectance. Implementing these methods into an apparatus, can include handheld devices, which can be used to measure water status by transmitting a terahertz signal through individual leaves or other plant tissues.

Additionally, as noted above, methods can be implemented to measure water status using terahertz reflectance. A number of embodiments utilize terahertz reflectance to measure water status of individual plants. By using terahertz reflectance, higher throughput methodologies can be developed that measure entire fields, greenhouses, forests, or other stands. Such of these embodiments are deployed as drone-mounted systems, thus allowing autonomous, semi-autonomous, or manually controlled terahertz imaging over a plant stand, field, forest, etc. Advantages of drone-based systems allow for the terahertz imaging on demand or short notice with little set up costs. Additional embodiments are mounted using cables, rails, or another mounting system that allows terahertz imaging. Such mounted systems can be mounted over fields, inside greenhouses, or on any other system where monitoring could occur on a regular or routine basis. Advantages of mounted systems include that these systems allow for monitoring with little to no damage or effects from drone propellers or other thrust or lift system.

A number of embodiments are configured to achieve strong reductions in water expenditure by coupling terahertz imagers with irrigation systems. In such systems, irrigation systems can be coupled to manual (e.g., handheld) or automated (e.g., drone mounted, rigged, stationary) terahertz devices. Some of these embodiments include controllers to control the irrigation process based on the water status of a plant these irrigation systems include water distribution systems, such as sprinklers, sprayers, and/or linear irrigation systems (including linear pivots). By coupling terahertz devices and irrigation systems in many embodiments, the water status determination and irrigation control is controlled using dynamic machine learning algorithms that can determine the water status of plants with high precision, enabling only the use of water required for the growth of plants at maximum productivity. Such systems provide water conservation and crop yield enhancement simultaneously. In such settings, the acquired terahertz scanner data is processed using machine learning algorithms in combination with other environmental parameters for efficient irrigation such that water expenditure is reduced while maximizing plant productivity.

Additional embodiments use machine learning algorithms to identify semantic similarities between the terahertz scan results and the plant water status parameters that are directly measured from extracted leaves. Specifically, statistical models and machine learning algorithms are used to find the unique relevance between frequency-dependent lead reflectance and transmittance at terahertz frequencies and WMA over different species. This function would be unique for each plant species. Therefore, by conducting calibration measurements on various excised leaves from different species, this unique function can be obtained and used for assessing the WMA of different plants of these species using terahertz scanning non-invasively.

Further embodiments apply machine learning algorithms with different regression and regularization methods. Such embodiments are able to determine the plant water status with confidence bounds that are a function of the terahertz measurement parameters, such as the frequency dependent parameters described herein, and modalities used for the water status determinations. By providing greater amounts of data in the disclosed analysis algorithms, plant water status determinations can be improved.

Even more embodiments utilize terahertz scanners to determine whether the plant is vegetative or generative by developing our novel algorithms through machine learning from the comparison of the terahertz experiment results, plant water status and other recorded environmental data. Such machine learning algorithms statistically learn from the large data sets that are created by the terahertz scanner and other recorded environmental data to automatically determine the water status and plant vegetative/generative states across various species at a wide range of dehydration states. Machine learning algorithms allow for the learning of statistical similarities that can capitalize on the available knowledge to enable active sensing.

EXEMPLARY EMBODIMENTS

Although the following embodiments provide details on certain embodiments of the inventions, it should be understood that these are only exemplary in nature, and are not intended to limit the scope of the invention.

EXAMPLE 1: Determining Water Status Variables in Various Stages of Dehydration BACKGROUND: Prior work has been able to invasively detect water status variables (e.g., WMA, RWC, and $\Psi_{leaf}$ while non-invasive methods have been limited to the prediction of WMA (or "equivalent water thickness") and RWC in hydrated leaves. Since no work has shown the ability to detect all water status variables (e.g., WMA, RWC, and $\Psi_{leaf}$) in stages of dehydration, the current ability to determine plant health or dehydration level is greatly limited, except using invasive and destructive methods.

: Plant material and sample preparation: Measurements were conducted on three species diverse in phylogeny, habitat type and responses to drought: *Arabidopsis thaliana* (Col-0), *Hedera canariensis*, and *Platanus racemosa* (Table 1). Large individuals of climber *H. canariensis*, and tree *P. racemosa* were sampled on and around the campus of the University of California, Los Angeles. *A. thaliana* Col-0, an annual herb, was grown in a climate-controlled greenhouse at the University of California, Los Angeles (minimum, mean and maximum values for temperature, 18.3° C., 22.4° C., 35.7° C.; for relative humidity 8.3%, 44.4%, 83.8%; and for irradiance 1.2, 67.6, 1296.2 µmol photons m-2 s-1). Seeds were cold-acclimated at 4° C. for three days and sown in pots (7.95 cm width×12.40 cm length×5.87 cm deep) in soil (1:1:2:1:1 mixture of washed plaster sand, loam, peat moss, perlite, vermiculite). After approximately a week, plants were thinned to one individual per pot, and plants were used after 5-6 weeks of growth.

For *H. canariensis* and *P. racemosa*, shoots with at least six fully developed leaves were harvested in the afternoon of the day prior to measurements and transported to the lab in plastic bags with wet paper towels. From each shoot, two nodes were recut under deionized water, and shoots were rehydrated overnight under plastic. For *A. thaliana*, trays of potted individuals were watered to saturation with deionized water and sealed with a dark plastic cover and wet paper towels for overnight rehydration. Two leaves from each of 3 individuals of *H. canariensis* and *P. racemosa*, and one leaf from each of five individuals of *A. thaliana* (a sixth leaf was not successful) were used for measuring terahertz transmission and leaf water status during dehydration.

Terahertz time-domain spectroscopy: A Ti:Sapphire laser (Coherent MIRA-HP, Coherent Inc., Santa Clara, USA) was used to generate femtosecond optical pulses at a 780 nm wavelength (FIG. 1). The beam of light was split into two, with the first beam used to pump a terahertz source to generate terahertz pulses, which were guided and focused on a terahertz detector, and the second beam passed through a linear delay stage to the terahertz detector. Plasmonic photoconductive nano-antenna arrays were used as the terahertz source and detector to provide high power terahertz radiation and high terahertz detection sensitivity over a broad terahertz frequency range. (See e.g., Yardimci and Jarrahi, (2017, cited above); and Yardimci et al., (2015,cited above).) By moving the linear delay stage and changing the time delay between the optical pump and probe pulses incident on the terahertz source and detector, respectively, the time-domain electric field profile of the terahertz pulses incident on the terahertz detector was resolved with a sub-picosecond resolution over a 400 ps time-window. Lock-in detection was used to increase the signal-to-noise ratio of the resolved signal. To further increase the signal-to-noise-ratio of the resolved signal, 10 time-domain traces were captured and averaged. By taking the Fourier transform of the averaged time-domain signal, the frequency-domain data were obtained with a 2.5 GHz frequency resolution (FIG. 2). The THz-TDS system used for the measurements reported in this work offered a 100-dB dynamic range and a frequency range of 0.1-5.5 THz.

Measurements of dehydrating leaves for terahertz transmission and leaf water status: Before starting measurements with the THz-TDS system, a reference signal was acquired without placing any leaf samples on the terahertz beam path.

To determine the potential influence of variation in the angle of terahertz radiation incident on the leaf samples, leaves of $H.$ $canariensis$ were measured at 90°, perpendicular to the beam, as well as at ±5.0° off the perpendicular direction. Negligible changes in the terahertz measurement results within this angle range.

Hydrated leaves were sealed in bags (Whirl-Pak, Nasco, Fort Atkinson, Wisconsin, USA) that had been exhaled into to generate a moist, high $CO_2$ environment to minimize transpiration, and placed in a larger plastic bag with wet paper towels to equilibrate at least 30 mins before weighing with an analytical balance (0.01 mg; MS205DU Mettler Toledo, Toledo, Ohio). Then, each leaf sample was placed on a motorized XY translation stage and the position of the leaf was adjusted such that a section of lamina between two secondary veins was exposed to the terahertz radiation. A collimated terahertz beam with ~1.5 cm-diameter beam spot size was used for the $H.$ $canariensis$ and $P.$ $racemosa$ leaves. The smaller and more fragile leaves of $A.$ $thaliana$ were placed on a glass slide to ensure proper alignment during dehydration, and the terahertz beam was focused to have a ~3 mm-diameter beam spot size for the measurements (FIG. 1).

Figure 4A:
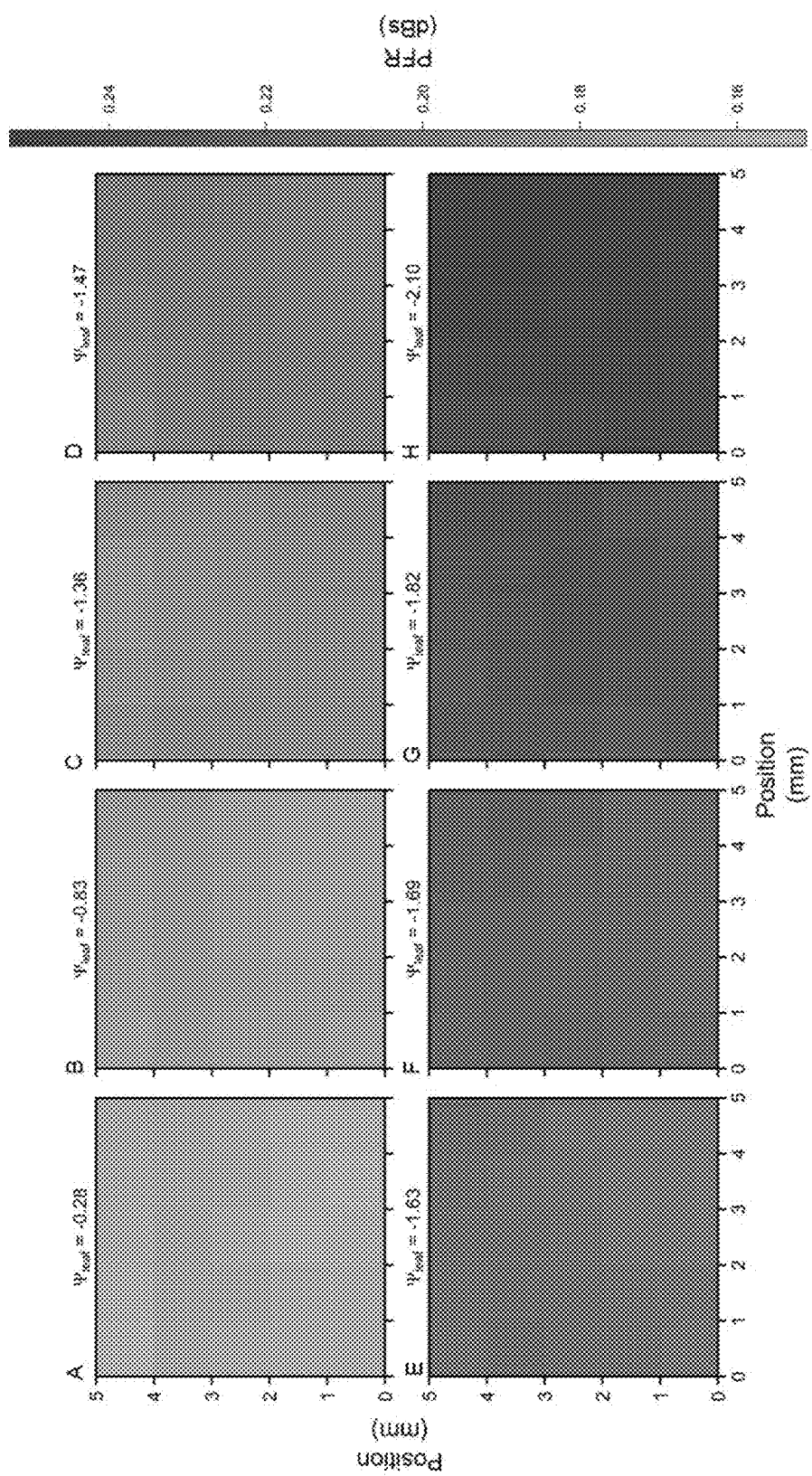
FIG. 4A illustrates terahertz transmission as a function of dehydration in accordance with various embodiments of the invention.

The measurements with the THz-TDS system were repeated for each leaf during dehydration, with the position of the terahertz beam on the leaves marked to return to approximately the same spot for each measurement. However, given that leaves were removed from the system and replaced for repeated measurements, there were shifts in the exact position of the terahertz beam on the leaf sample in successive measurements; thus, for each dehydration stage, 25 measurements (at 1 mm steps) were made within the marked 5×5 $mm^2$ area for each $H.$ $canariensis$ and $P.$ $racemosa$ sample and averaged to improve the precision of the mean (FIG. 4A). Since a beam with much smaller spot size was incident on $A.$ $thaliana,$ 169 measurements (at 0.5 mm steps) were taken within a 6×6 $mm^2$ area. The THz-TDS system can image the leaf surface with even greater resolution (FIG. 4B) but require significant measurement times which may result in greater than expected dehydration for excised tissues. After each THz-TDS measurement, the leaf and bag were weighed with the analytical balance, and $\Psi_{leaf}$ was determined with a pressure chamber (0.001 MPa resolution, Plant Moisture Stress Model 1000; PMS Instruments Co). Then, the leaves were bench dried on a fan to reduce $\Psi_{leaf}$ by 0.1-0.2 MPa, and the terahertz measurements were repeated. Once at least two measurements were completed below the species' previously published turgor loss point; (See e.g., Scoffoni et al., (2018, cited above); and Scoffoni et al., (2014) Leaf shrinkage with dehydration: coordination with hydraulic vulnerability and drought tolerance. Plant Physiology 164: 1772-1788; the disclosures of which are herein incorporated by reference in their entireties;) an image of the leaf was taken using a flatbed scanner (Epson Perfection 4490 Photo, Seiko Epson Corporation) and the leaf lamina area (LA) was determined using Fiji (Schindelin et al., 2012). After the experiment, the mass of the bag was determined and subtracted for calculation of fresh leaf mass (FM) values for each leaf dehydration stage.

Leaf mass per area (LMA), relative water content (RWC), and saturated water content (SWC) were calculated as described above in reference to equations 13-15 and the surrounding text.

Species-specific pressure-volume curves were constructed using RWC and $\Psi_{leaf}$ data for the leaves that had more than three data points more negative than turgor loss point, i.e., for 3 leaves of $H.$ $canariensis$ and 5 leaves of $P.$ $racemosa.$ For $A.$ $thaliana,$ given the fewer data available for dehydration sequences of individual leaves, data for all six leaves were pooled together into an overall pressure-volume curve. (See e.g., Scoffoni et al., (2018, cited above).) From the pressure volume curves, parameters were extracted including turgor loss point ($\Psi_{tlp}$), osmotic potential at full turgor ($\Pi_o$), relative water content values at turgor loss point ($RWC_{tlp}$). (See e.g., Sack and Pasquet-kok, (2011, cited above).) When "plateau effects" were detected during early dehydration, i.e., minute changes in $\Psi_{leaf}$ despite substantial declines of leaf water, representing the dehydration of water-filled leaf airspaces, these points were removed before estimation of pressure-volume parameters. (See e.g., Kubiske and Abrams, (1990) Pressure-volume relationships in non-rehydrated tissue at various water deficits. Plant, Cell & Environment 13: 995-1000; the disclosure of which is herein incorporated by reference in its entirety.)

Figure 5:
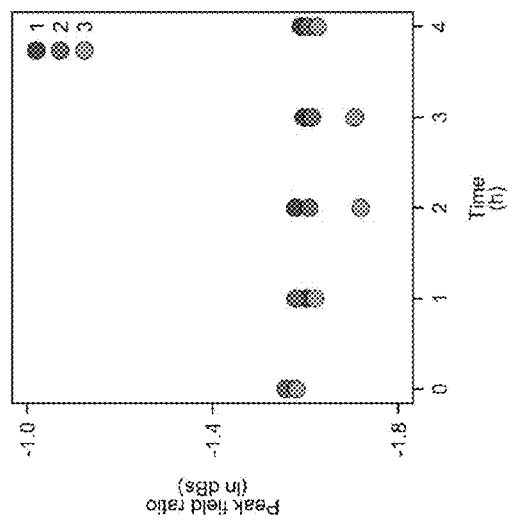
FIG. 5 illustrates an influence of time on terahertz transmission for leaves maintained at full hydration in accordance with various embodiments of the invention.

A control was established to ensure that the change in the measured terahertz pulse during leaf dehydration was due to declining leaf water status, rather than simply associated with time duration. Thus, for $H.$ $canariensis,$ leaves that were maintained fully hydrated were measured over time (FIG. 5). Shoots of $H.$ $canariensis$ were rehydrated, and then leaves were excised near the base of the petiole in a petri dish under filtered ultra-pure degassed water (0.22 μm Thornton 200 CR; Millipore). The petioles were wrapped in parafilm and connected under filtered water to clear polyvinyl chloride tubing containing filtered water. Terahertz transmission measurements were recorded for these leaves at 1 h intervals for 4h. For each measurement, the leaves were removed, weighed for determination of RWC and reconnected to the tubing under water. Leaf dry mass was determined after oven drying for 48h at 70° C. No variation was found in terahertz absorption over time for the hydrated leaves (FIG. 5).

A physically-based model for leaf water status from terahertz signal analysis: During the terahertz measurements, the electromagnetic radiation was partially reflected from the leaf surface and partially absorbed within the leaf. The absorbed terahertz radiation can be estimated by comparing the time-domain reference signal with that obtained after transmission through the leaf. The peak field ratio (PFR) used to estimate leaf water status (FIG. 5b) was calculated in accordance with equations 1-12 and the surrounding text.

Based on the relationship of water mass per area (WMA) to ln (PFR) (Equation 8), determinations are made of water mass per area $\overline{WMA}$. Then, relative water content $\overline{RWC}$ is estimated, including saturated water mass per leaf area (SWMA), which is the product of leaf dry mass per area (LMA) and saturated water content (SWC) (Equations 8 and SWMA=LMA SWC). Finally, leaf water potential $\overline{\Psi_{leaf}}$ is estimated using pressure volume curve (PV) parameters (Equations 10-12).

Figure 4B:
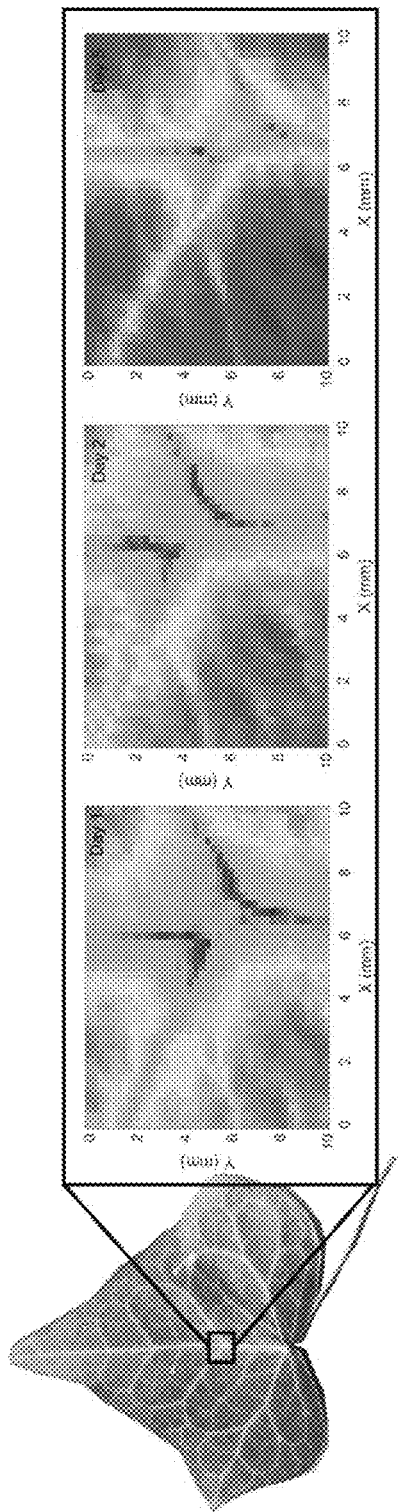
FIG. 4B illustrates images of leaf water thickness during dehydration in accordance with various embodiments of the invention.

Statistics: Applying this physically-based model statistically, this embodiment used measured terahertz spectroscopy peak field ratio (PFR) to determine leaf water status variables, leaf water mass per area ($\overline{WMA}$), relative water content (RWC), and leaf water potential ($\overline{\Psi_{leaf}}$) Determinations were made for each individual leaf during dehydration (Table 2, left column), based on the relationship of water mass per area (WMA) to In (PFR) for each dehydrating leaf, and from individual leaf values for saturated water mass per leaf area (SWMA) and species-level mean pressure-volume curve (PV) parameters. Determinations were also tested using species-level relationships of WMA to In (PFR) (Table 2, middle column) and all-species-level relationships of WMA to In (PFR) (Table 2, right column), using species-level mean values for SWMA and PV parameters. These estimates were the tested to determine the correspondence to observed values of WMA, RWC and $\Psi_{leaf}$ (FIG. 4B).

To estimate the relationships of In (PFR) to WMA at individual leaf, or species, or all-species scale, lines were fitted using ordinary least squares (OLS) regression with the fir function in the stats R package (R Core Team, (2019) R: A language and environment for statistical computing. In, Ed 3.6.1. R Foundation for Statistical Computing, Vienna, Austria; the disclosure of which is herein incorporated by reference in its entirety.) Similarity of slopes were tested among leaves of each species in the relationships of In (PFR) and WMA by performing an analysis of covariation (AN-COVA) (e.g., using SMATR). Further, similarity of slopes were tested for across species, considering all leaves of each species together.

In applying the hierarchical approach to determination, from $\overline{WMA}$ to $\overline{RWC}$ to $\overline{\Psi_{leaf}}$, outlier points that represented impossible values were removed for higher-level determinations. (See e.g., Riazoshams et al. (2019) Robust Nonlinear Regression. Wiley, Hoboken New Jersey, USA; the disclosure of which is herein incorporated by reference in its entirety.) Thus, when high outliers for $\overline{WMA}$ from the fitted relationship of WMA to In (PFR) led, when scaled by SWMA, to $\overline{RWC}$ values that exceeded 1.0 g·g$^{-1}$, and to $\overline{\Psi_{leaf}}$ values that exceeded 0 MPa, or when extremely negative $\overline{\Psi_{leaf}}$ were determined from $\overline{RWC}$ values far below the range of values in the PV curve, these $\overline{RWC}$ and $\overline{\Psi_{leaf}}$ values were removed for the estimation of determinative capacity. Altogether, for estimation of determinative capacity at the individual leaf level, values for 3 of 38 leaves were removed for *H. canariensis* and 1 of 42 leaves for *P. racemosa*; at the species level, 7 of 42 leaves for *P. racemosa*; and at the all-species level, 8 of 38 leaves for *H. canariensis*, and 21 of 42 leaves for *P. racemose*.

Model determinations of leaf water status at leaf-scale were tested, at species-scale and at all species scale, by plotting estimated against observed values, and calculating R$^2$ and root mean square error (RMSE, in the same units as the predicted variable) as:

$$RMSE = \sqrt{(observed - predicted)^2} \tag{16}$$

To compare the error in determining different water status variables across scales, a normalized RMSE were also calculated (i.e., NRMSE). (See e.g., Botchkarev, (2018) Performance metrics (error measures) in machine learning regression, forecasting and prognostics: properties and typology. arXiv preprint arXiv:1809.03006; the disclosure of which is herein incorporated by reference in its entirety.)

$$NRMSE = \frac{RMSE}{y_{max} - y_{min}} \tag{17}$$

Figure 7:
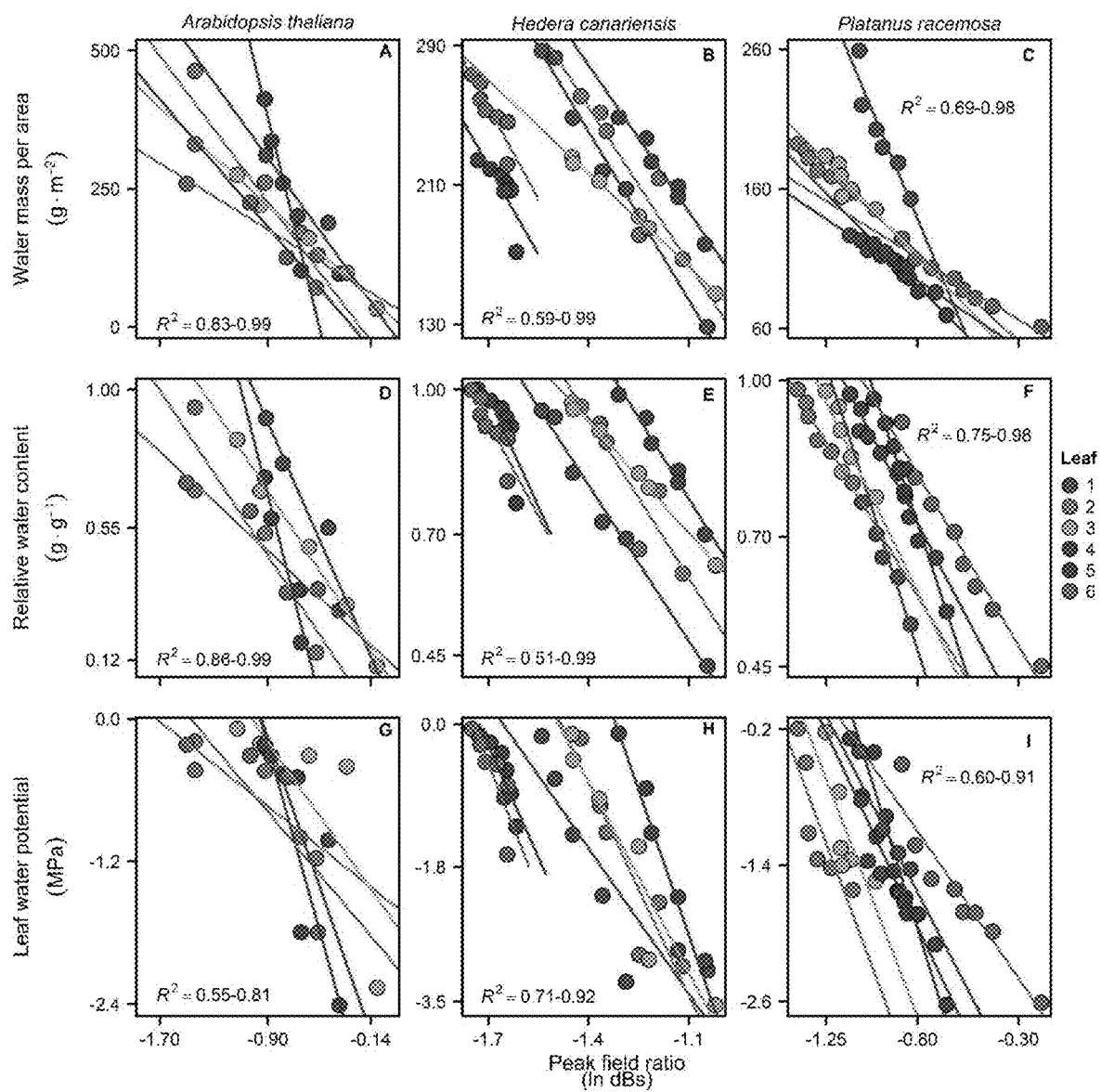
FIG. 7 illustrates an association of water status variables with the terahertz transmission peak field ratio for three species in accordance with various embodiments of the invention.
Figure 8:
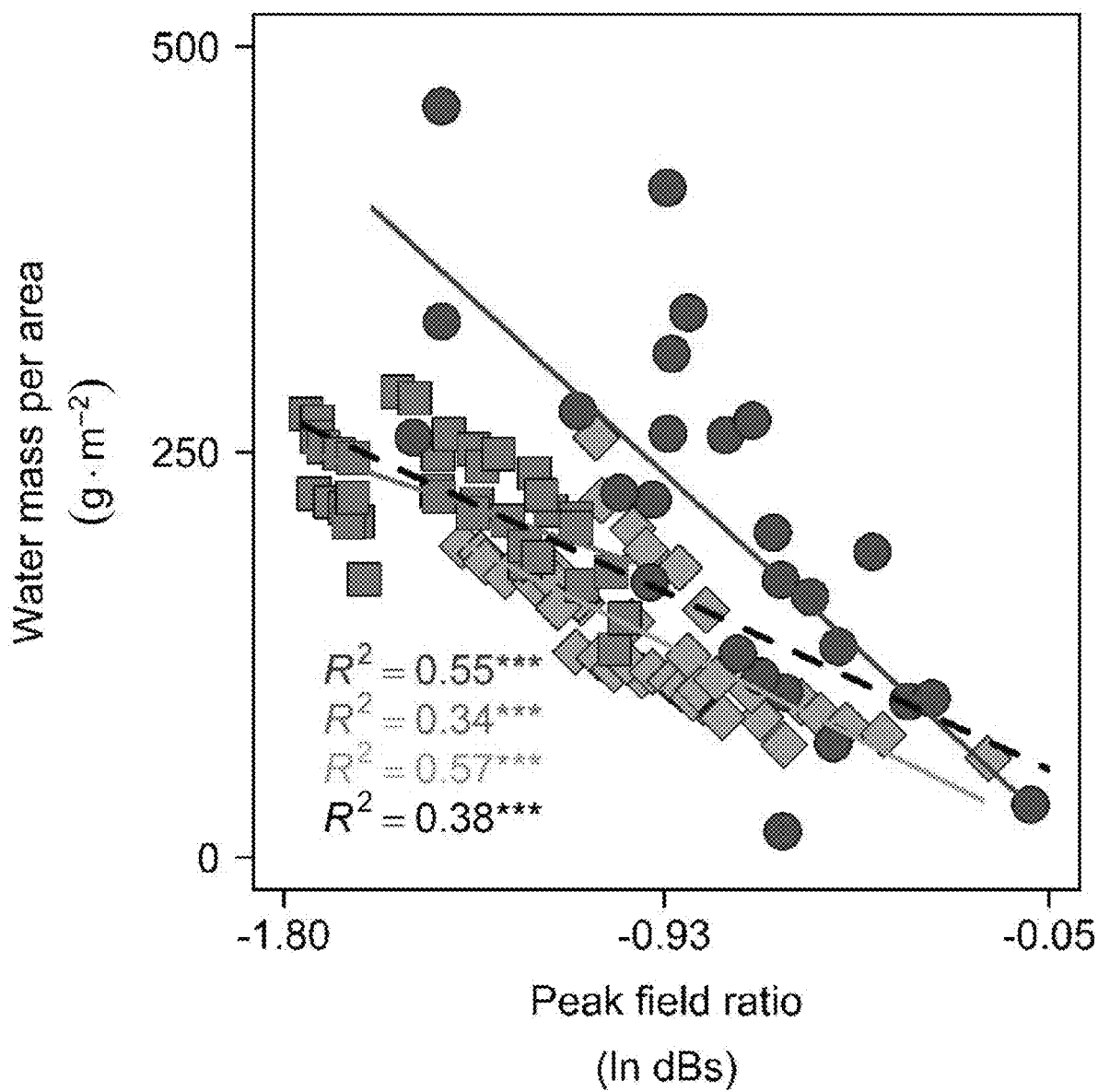
FIG. 8 illustrates an association of water mass per area with the terahertz transmission peak field ratio, generalizing across leaves within and across three species in accordance with various embodiments of the invention.

RESULTS: Terahertz measurements showed strong ability to determine all three leaf water status variables, supporting the physically-based model for the relationship of WMA with In (PFR). As leaf water status declined, terahertz transmission increased, and for individual leaves the decline of WMA, RWC, and $\Psi_{leaf}$ were associated with In (PFR) across the range from full turgor to $\Psi_{tlp}$ and below $\Psi_{tlp}$ (FIG. 7; Table 3). Notably, the relationships for individual leaves of WMA, RWC and $\Psi_{leaf}$ with In (PFR) differed significantly in slopes and intercepts (Table 3). Despite the variation among leaves of given species, the relationship of WMA with In (PFR) was strong combining leaves for given species, or even across species (FIG. 8).

Figure 6:
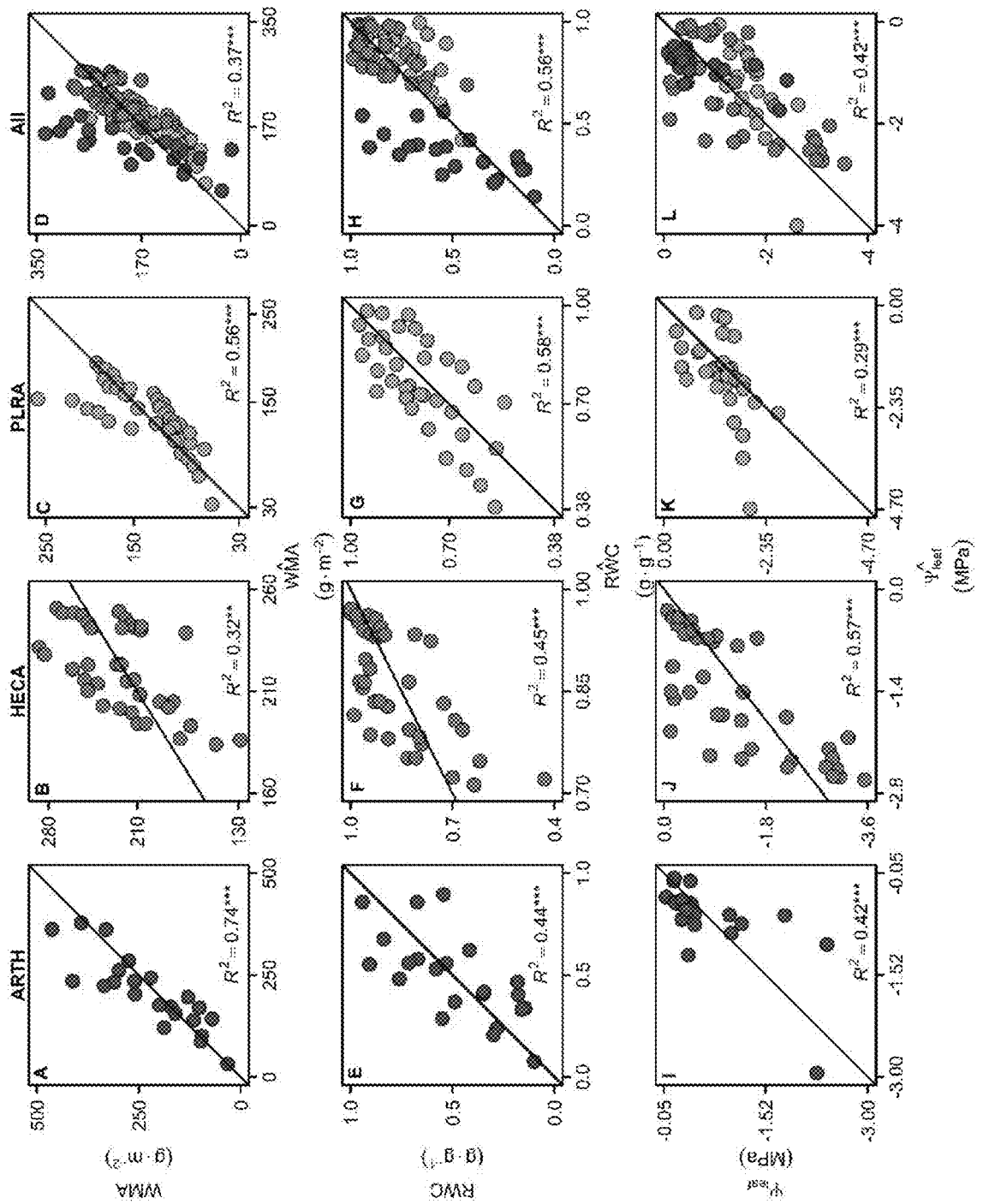
FIG. 6 illustrates a species-specific determinations of leaf water status using terahertz spectroscopy in accordance with various embodiments of the invention.
Figure 9:
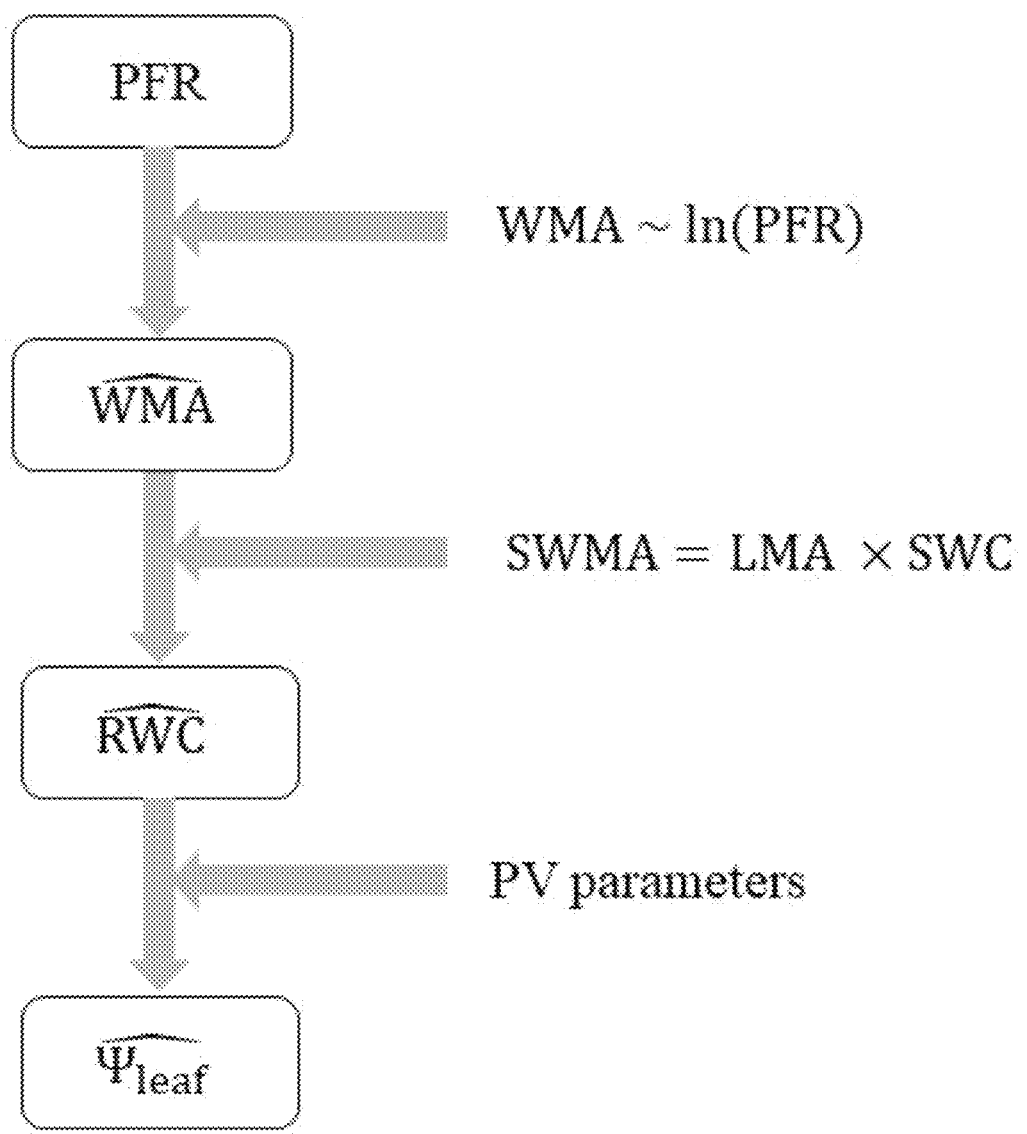
FIG. 9 illustrates a flow chart illustrating the inputs to for the hierarchical determination of water status variables from terahertz spectroscopy peak field ratio and leaf traits in accordance with various embodiments of the invention.

Given these strong relationships, leaf water status variables could be determined across scales, from individual leaf, to species, to all-species, using our hierarchical approach to estimation (Table 4; FIG. 9). Thus, for given leaves, or for a given species, or across all species, $\overline{WMA}$ could be determined from the relationship with In (PFR) (FIGS. 6A-6C), relative water content ($\overline{RWC}$) could be determined by additionally including leaf- or species-level means for saturated water mass per unit leaf area (SWMA) (FIGS. 6E-6G), and $\overline{\Psi_{leaf}}$, by additionally including pressure-volume curve parameters (FIGS. 6I-6K). As expected, the error in determining WMA, RWC and $\Psi_{leaf}$ increased across these scales of variation, i.e., from individual leaf to species (FIG. 7; FIGS. 6A-6L). Further, the error increased from determination of $\overline{WMA}$ and $\overline{RWC}$ to $\overline{\Psi_{leaf}}$ as indicated by higher NRMSE values (Table 4; FIGS. 6A-6L). The goodness of fit (i.e., significant R$^2$ values) and determinative power (i.e., relatively low RMSE and NRMSE) values; Table 4) signified strong potential for estimation of all three water status variables using the physically-based model and hierarchical determination approach within and across species (Table 2; FIG. 9).

CONCLUSION: This exemplary embodiment identifies strong relationships of leaf water status variables (WMA, RWC, and $\Psi_{leaf}$) transmission of terahertz radiation for three diverse species. The work further shows a strong association of terahertz absorption with water status within the range of operating leaf water status, i.e., between full turgor and turgor loss point and below turgor loss point. This embodiment further extends prior work to determine $\Psi_{leaf}$ beyond past just the prediction of just WMA (or "equivalent water thickness") and RWC and enables the translation of terahertz measured PFR to all three water status variables, which could be extended to the detection of leaf water status using other ranges of wavelengths.

This embodiment further indicates the potential to extend water status determination across multiple leaves of given species, and even across multiple species, assuming knowledge of additional leaf traits, such as leaf mass per area (LMA), saturated water content (SWC) and pressure-volume parameters. This finding highlights the great potential for the expansion of the use of terahertz transmission to determine water status non-invasively for individual leaves, and also across canopies and indeed, mixed canopy ecosystems.

Doctrine of Equivalents

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all

TABLE 1

Species are listed with family, geographic origin, growth habit and calculated pressure volume curve parameters, including water potential at turgor loss point ($\Psi_{tlp}$), modulus of elasticity ($\varepsilon$), osmotic potential at full turgor ($\pi_o$) and the relative water content at turgor loss point ($RWC_{tlp}$).

| Species | Family | Origin | Plant Habit | $\Psi_{tlp}$ MPa | $\varepsilon$ MPa | $\pi_o$ at full turgor MPa | $RWC_{tlp}$ % |
|---|---|---|---|---|---|---|---|
| *Arabidopsis thaliana* | Brassicaceae | Pan-Mediterranean | Herbaceous | −0.41 | 0.26 | −0.28 | 67.2 |
| *Hedera canariensis* | Araliaceae | Canary Islands | Climber | −2.32 | 7.85 | −1.71 | 78.3 |
| *Platanus racemosa* | Platanaceae | Southern California | Tree | −1.39 | 9.69 | −1.16 | 86.4 |

TABLE 2

Inputs for using measured terahertz spectroscopy peak field ratio (PFR) to determine leaf water status variables, water mass per area ($\widehat{WMA}$), relative water content ($\widehat{RWC}$), and leaf water potential ($\widehat{\Psi_{leaf}}$). Determinations were made for each individual leaf during dehydration ($\widehat{WMA}_{leaf}$, $\widehat{RWC}_{leaf}$ and $\widehat{\Psi}_{leaf,leaf}$, left column), based on the relationship of water mass per area (WMA) to ln(PFR) for each dehydrating leaf, and from individual leaf values for saturated water mass per leaf area (SWMA) and species-level mean pressure-volume curve (PV) parameters. Determinations were also tested using species-level relationships of WMA to ln(PFR) ($\widehat{WMA}_{species}$, $\widehat{RWC}_{species}$ and $\widehat{\Psi}_{leaf,species}$, middle column) and all-species-level relationships of WMA to ln(PFR) ($\widehat{WMA}_{all}$, $\widehat{RWC}_{all}$ and $\widehat{\Psi}_{leaf,all}$, right column), using species-level mean values for SWMA and PV parameters.

| | Individual leaf level determination | Species-level determination | All species-level determination |
|---|---|---|---|
| $\widehat{WMA}$ | $\widehat{WMA}_{leaf}$, from WMA~ln (PFR) relationship for each leaf | $\widehat{WMA}_{species}$, from WMA~ln (PFR) relationship for all leaves of given species | $\widehat{WMA}_{all}$, from WMA~ln (PFR) relationship for all leaves of all species |
| $\widehat{RWC}$ | $\widehat{RWC}_{leaf}$, from $\widehat{WMA}_{leaf}$ and SWMA of each leaf | $\widehat{RWC}_{species}$ from $\widehat{WMA}_{species}$ and SWMA: species-level mean | $\widehat{RWC}_{all}$ from $\widehat{WMA}_{all}$ and SWMA: species-level means |
| $\widehat{\Psi}_{leaf}$ | $\widehat{\Psi}_{leaf,leaf}$, from $\widehat{RWC}_{leaf}$ and P-V parameters: species-level mean | $\widehat{\Psi}_{leaf,species}$, from $\widehat{RWC}_{species}$ and P-V parameters: species-level mean | $\widehat{\Psi}_{leaf,all}$, from $\widehat{RWC}_{all}$ and P-V parameters: species-level mean |

TABLE 3

Ordinary least squares (OLS) regression model parameters with lower and upper confidence intervals (CI) and tests of common slope (ANCOVA) among leaves. Relationships for each leaf, species, and across multiple species of water mass per area (WMA) with terahertz transmission (ln PFR) were tested and used to determine relative water content and leaf water potential. P-values for individual leaves represent the fit of the linear model, and for common slopes, represent a test for the significance of variation in slope among individual leaves or among species.

| Species | Leaf | Slope (Lower CI, Upper CI) | Intercept (Lower CI, Upper CI) | $R^2$ | p value |
|---|---|---|---|---|---|
| *Arabidopsis thaliana* | 1 | −343 (−656, −30.2) | −3.24 (−210, 203) | 0.88 | 0.0421 |
| | 2 | −332 (−566, −97.0) | −72.8 (−320, 174) | 0.83 | 0.0205 |
| | 3 | −223 (−263, −182) | 19.7 (−8.57, 48.0) | 0.99 | 0.000400 |
| | 4 | −1002 (−1727, −277) | −521 (−1095, 49.9) | 0.95 | 0.0277 |
| | 5 | −312 (−582, −42.7) | −63.0 (−333, 207) | 0.93 | 0.038 |
| *A. thaliana* common slope | | | | | 0.0370 |
| *Hedera canariensis* | 1 | −322 (−377, −268) | −211 (−286, −135) | 0.99 | <0.0001 |
| | 2 | −300 (−496, −103) | −165 (−417, 87.8) | 0.82 | 0.0130 |
| | 3 | −179 (−193, −164) | −33.3 (−51.9, −14.6) | 0.99 | <0.0001 |
| | 4 | −281 (−357, −205) | −114 (−203, −24.4) | 0.96 | 0.001 |
| | 5 | −340 (−664, −16.4) | −357 (−895, 181) | 0.59 | 0.043 |
| | 6 | −353 (−575, −132) | −3.45 (−721, 30.2) | 0.77 | 0.009 |
| *H. canariensis* common slope | | | | | 0.001 |
| *Platanus racemosa* | 1 | −347 (−523, −172) | −139 (−311, 33.3) | 0.85 | 0.005 |
| | 2 | −128 (−164, −91.1) | 13.0 (−33.9, 59.8) | 0.95 | <0.001 |
| | 3 | −151 (−272, −30.6) | −9.70 (−149, 130) | 0.69 | 0.025 |
| | 4 | −97.1 (−110, −84.5) | 16.9 (4.90, 29.0) | 0.98 | <0.0001 |
| | 5 | −147 (−173, −122) | −27.5 (−49.5, 50.0) | 0.97 | <0.0001 |
| | 6 | −89.5 (−107, −72.3) | 39.4 (28.6, 50.2) | 0.96 | <0.0001 |
| *P. racemosa* common slope | | | | | 0.003 |
| *Arabidopsis thaliana* | | −133 (−172, −96.5) | 82.0 (−28.5, 44.9) | 0.55 | $1.28 \cdot 10^{-5}$ |

TABLE 3-continued

Ordinary least squares (OLS) regression model parameters with lower and upper confidence intervals (CI) and tests of common slope (ANCOVA) among leaves. Relationships for each leaf, species, and across multiple species of water mass per area (WMA) with terahertz transmission (ln PFR) were tested and used to determine relative water content and leaf water potential. P-values for individual leaves represent the fit of the linear model, and for common slopes, represent a test for the significance of variation in slope among individual leaves or among species.

| Species | Leaf | Slope (Lower CI, Upper CI) | Intercept (Lower CI, Upper CI) | $R^2$ | p value |
|---|---|---|---|---|---|
| Hedera canariensis | | −91.7 (−135, −48.6) | 90.3 (28.0, 153) | 0.34 | 0.0001 |
| Platanus racemosa | | −245 (−339, −151) | 90.0 (−71.7, 89.7) | 0.57 | $9.17 \cdot 10^{-9}$ |
| All species | | −125 | 48.0 | 0.38 | $2.25 \cdot 10^{-12}$ |
| All-species common slope | | | | | 0.022 |

TABLE 4

Determinative power for the determination of water mass per area (WMA), relative water content (RWC), and leaf water potential ($\Psi_{leaf}$), from terahertz spectroscopy, including the root mean square error (RMSE), the $R^2$, and the normalized RMSE (NRMSE), for individual leaves of each species (with minimum, mean and maximum values reported), and using species-specific relationships, and the all-species relationship (Table 2; FIG. 9).

| Species code | Variable | RMSE (min-mean-max) | $R^2$ (min-mean-max) | NRMSE (min-mean-max) |
|---|---|---|---|---|
| Individual leaf level determination | | | | |
| Arabidopsis thaliana | WMA | 8.43-28.0-48.2 | 0.80-0.89-0.99 | 0.347-0.0942-0.123 |
| | RWC | 0.0254-0.0597-0.0981 | 0.80-0.89-0.99 | 0.0344-0.0940-0.123 |
| | $\Psi_{leaf}$ | 0.0223-0.200-0.371 | 0.49-0.76-0.92 | 0.0762-0.130-0.235 |
| Hedera canariensis | WMA | 1.55-7.57-15.0 | 0.80-0.80-0.80 | 0.0199-0.104-0.193 |
| | RWC | 0.00670-0.0284-0.0553 | 0.80-0.80-0.80 | 0.0199-0.101-0.185 |
| | $\Psi_{leaf}$ | 0.174-0.256-0.339 | 0.70-0.70-0.70 | 0.0665-0.112-0.170 |
| Platanus racemosa | WMA | 1.67-4.71-11.4 | 0.80-0.80-0.80 | 0.0410-0.0828-0.173 |
| | RWC | 0.0122-0.0246-0.0398 | 0.80-0.80-0.80 | 0.0411-0.0829-0.173 |
| | $\Psi_{leaf}$ | 0.0680-0.170-0.225 | 0.70-0.70-0.70 | 0.0305-0.115-0.176 |
| Species-level determination | | | | |
| Arabidopsis thaliana | WMA | 58.7 | 0.74 | 0.136 |
| | RWC | 0.184 | 0.44 | 0.218 |
| | $\Psi_{leaf}$ | 0.487 | 0.42 | 0.209 |
| Hedera canariensis | WMA | 28.9 | 0.32 | 0.182 |
| | RWC | 0.0935 | 0.45 | 0.164 |
| | $\Psi_{leaf}$ | 0.703 | 0.57 | 0.202 |
| Platanus racemosa | WMA | 29.8 | 0.56 | 0.151 |
| | RWC | 0.0841 | 0.58 | 0.159 |
| | $\Psi_{leaf}$ | 0.425 | 0.29 | 0.175 |
| All species-level determination | | | | |
| All species | WMA | 61.6 | 0.37 | 0.138 |
| All species | RWC | 0.151 | 0.56 | 0.159 |
| All species | $\Psi_{leaf}$ | 0.700 | 0.42 | 0.201 |

What is claimed is:

1. A terahertz plant tissue sensing system, comprising:
a terahertz source configured to generate a terahertz beam having a frequency of approximately 100 GHz to approximately 10 THz;
a terahertz detector configured to receive and record a terahertz signal;
at least one optical element to guide the terahertz beam along an optical path from the terahertz source to the terahertz detector, where the optical path impinges on a target plant tissue to generate a signal from the target plant tissue; and
an analyzer to determine at least one water status variable of the target plant tissue based on a field intensity of the signal from the target plant tissue and a field intensity of a reference signal,
wherein the at least one water status variable selected from the group consisting of water mass per area, relative water content, and water potential,
wherein the water mass per area is determined as a function of the field intensity of the signal from the target plant tissue and the field intensity of the reference signal;
wherein the relative water content is determined as a ratio between water mass per area and a saturated water mass per area; and
wherein the water potential ($\Psi_{leaf}$) is determined according to at least one selected from a group consisting of:
a pre-defined calibration curve; and
a sum of a solute potential and a pressure potential.

2. The system of claim 1, further comprising a light source configured to generate an optical pulse focused to impinge the terahertz source, and wherein the terahertz beam is a terahertz pulse.

3. The system of claim 2, wherein the light source is a femtosecond laser.

4. The system of claim 2, further comprising a splitter and a delay stage, wherein the optical pulse passes through the splitter allowing a first beam to impinge the terahertz source and allowing a second beam passes through the delay stage en route to the terahertz detector.

5. The system of claim 2, further comprising:
a two-dimensional stage, wherein the target plant tissue is moved in two dimensions;
wherein the terahertz source generates a plurality of terahertz beams, such that each beam in the plurality of terahertz beams impinges on a different location on the target plant tissue.

6. The system of claim 1, wherein at least one of the terahertz source and the terahertz detector is a plasmonic photoconductive nano-antenna array.

7. The system of claim 1, wherein the function of the field intensity of the signal from the target plant tissue and the field intensity of the reference signal is determined by obtaining a plurality of terahertz measurements from a plurality of leaves.

8. The system of claim 7, wherein the function of the field intensity of the signal from the target plant tissue and the field intensity of the reference signal is statistically modeled to resolve the water mass per area.

9. The system of claim 8, wherein the statistical modeling is performed using an ordinary least squares regression.

10. The system of claim 1, wherein solute potential ($\Psi_S$) and pressure potential ($\Psi_P$) are calculated as:

$$\Psi_S = \frac{\pi_o \cdot \Psi_{tlp}(1 - RWC_{tlp})}{\pi_o(1 - RWC) + \Psi_{tlp}(RWC - RWC_{tlp})}$$

and:

$$\Psi_P = \begin{cases} \pi_o \cdot \left(\frac{RWC - RWC_{tlp}}{1 - RWC_{tlp}}\right), & \text{if } RWC > RWC_{tlp} \\ 0, & \text{if } RWC < RWC_{tlp} \end{cases}$$

where $\pi_o$, is the osmotic potential at full turgor, RWC is the determined relative water content, $\Psi_{tlp}$ is water potential at turgor los point, and $RWC_{tlp}$ the relative water content at turgor loss point.

11. A method for terahertz imaging of plant tissue, comprising:
illuminating a target plant tissue with a terahertz pulse to produce a signal therefrom, wherein the terahertz pulse has a frequency of approximately 100 GHz to approximately 10 THz;
detecting the signal using a terahertz detector; and
determining at least one water status variable based on a field intensity of the signal from the target plant tissue and a field intensity of a reference signal,
wherein the at least one water status variable selected from the group consisting of water mass per area, relative water content, and water potential;
wherein the water mass per area is determined as a linear function of the field intensity of the signal from the target plant tissue and the field intensity of the reference signal;

wherein the relative water content is determined as a ratio between water mass per area and a saturated water mass per area; and
wherein the water potential ($\Psi_{leaf}$) is determined according to at least one selected from a group consisting of:
a pre-defined calibration curve; and
a sum of a solute potential and a pressure potential.

12. The method of claim 11, further comprising generating the terahertz pulse by illuminating a terahertz source with a light source.

13. The method of claim 11, wherein the illuminating comprises illuminating the target plant tissue with a plurality of terahertz pulses, where each pulse in the plurality of terahertz pulses impinges on a different location on the target plant tissue.

14. The method of claim 11, wherein the function of the field intensity of the signal from the target plant tissue and the field intensity of the reference signal is determined by obtaining a plurality of terahertz measurements from a plurality of leaves.

15. The method of claim 14, wherein the function of the field intensity of the signal from the target plant tissue and the field intensity of the reference signal is statistically modeled to resolve the water mass per area.

16. The method of claim 15, wherein the statistical modeling is performed using an ordinary least squares regression.

17. The method of claim 11, wherein solute potential ($\Psi_S$) and pressure potential ($\Psi_P$) are calculated as:

$$\Psi_S = \frac{\pi_o \cdot \Psi_{tlp}(1 - RWC_{tlp})}{\pi_o(1 - RWC) + \Psi_{tlp}(RWC - RWC_{tlp})}$$

and:

$$\Psi_P = \begin{cases} \pi_o \cdot \left(\frac{RWC - RWC_{tlp}}{1 - RWC_{tlp}}\right), & \text{if } RWC > RWC_{tlp} \\ 0, & \text{if } RWC < RWC_{tlp} \end{cases}$$

where $\pi_o$, is the osmotic potential at full turgor, RWC is the determined relative water content, $\Psi_{tlp}$ is water potential at turgor los point, and $RWC_{tlp}$ is the relative water content at turgor loss point.

18. A plant tissue sensing system, comprising:
a plant tissue water content detection system, further comprising:
a source configured to generate a beam having a frequency of approximately 100 GHz to approximately 10 THz;
a detector configured to receive and record a signal; and
at least one optical element to guide the beam along an optical path from the source to the detector, where the optical path impinges on a target plant tissue to generate a signal from the target plant tissue; and
an analyzer to determine at least one water status variable of the target plant tissue based on a field intensity of the signal from the target plant tissue and a field intensity of a reference signal,
wherein the at least one water status variable selected from the group consisting of water mass per area, relative water content, and water potential,
wherein the water mass per area is determined as a function of the field intensity of the signal from the target plant tissue and the field intensity of the reference signal;

wherein the relative water content is determined as a ratio between water mass per area and a saturated water mass per area; and wherein the water potential ($\Psi_{leaf}$) is determined according to at least one selected from a group consisting of:
a pre-defined calibration curve; and
a sum of a solute potential and a pressure potential.

* * * * *